United States Patent
Paul et al.

(10) Patent No.: US 7,078,587 B1
(45) Date of Patent: Jul. 18, 2006

(54) TAPETUM-SPECIFIC PROMOTERS

(75) Inventors: Wyatt Paul, Aubiere (FR); Roderick John Scott, Bath (GB); Diane Hird, Bristol (GB); Rachel Hodge, Bath (GB)

(73) Assignee: Biogemma UK Limited, Cambridge (GB)

( * ) Notice: Subject to any disclaimer, the term of this patent is extended or adjusted under 35 U.S.C. 154(b) by 0 days.

(21) Appl. No.: 09/959,856

(22) PCT Filed: May 10, 2000

(86) PCT No.: PCT/GB00/01789

§ 371 (c)(1),
(2), (4) Date: May 14, 2002

(87) PCT Pub. No.: WO00/68403

PCT Pub. Date: Nov. 16, 2000

(30) Foreign Application Priority Data

May 10, 1999 (GB) .................................. 9910796.3

(51) Int. Cl.
*C12N 15/82* (2006.01)
*A01H 5/00* (2006.01)

(52) U.S. Cl. .................. 800/287; 536/24.1; 800/298; 435/252.3; 435/320.1; 435/419

(58) Field of Classification Search ............. 435/320.1, 435/419, 468, 252.3; 536/24.1; 800/287, 800/303, 298
See application file for complete search history.

(56) References Cited

U.S. PATENT DOCUMENTS 5,635,384 A 6/1997 Walsh et al. ................. 435/199

5,837,850 A 11/1998 Huffman .................... 536/24.1

FOREIGN PATENT DOCUMENTS

WO  WO 97/38116  10/1997

OTHER PUBLICATIONS

Kim et al. A 20 nucleotide upstream element is essential for the nopaline synthase (nos) promoter activity. Plant Molecular Biology, 1994, vol. 24, pp. 105-117.*
Eyal et al. Pollen specificity elements reside in 30 bp of the proximal promoters of two pollen-expressed genes. The Plant Cell, Mar. 1995, vol. 7, pp. 373-384.*
Database GenEMBL Accession No. AW057058, Walbot, V., "660008812.y1 660—Mixed stages of anther and pollen Zea Mays cDNA, mRNA sequence," (Oct. 6, 1999).
Database GenEMBL Accession No. AW562916, Walbot, V., "660069F07.x1 660—Mixed stages of anther and pollen Zea mays cDNA, mRNA sequence" (Mar. 15, 2000).
International Search Report for International Application No. PCT/GB00/01789, mailed Apr. 3, 2001.

* cited by examiner

*Primary Examiner*—Cynthia Collins
(74) *Attorney, Agent, or Firm*—Sterne, Kessler, Goldstein & Fox P.L.L.C.

(57) ABSTRACT

The present invention relates to nucleic acid sequences encoding tapetum specific promoters, for use in Artificial Male Sterility systems in plants. In particular, the promoters may be the pMAC2 promoter; the pMAC20 promoter; or promoter sequences which naturally controls the expression of a coding sequence substantially homologous to the MAC2 or MAC20 coding sequences. Also provided are regulatory elements of the promoters; plant cells and plants transformed with the promoter sequences.

14 Claims, 19 Drawing Sheets

Mac2 RT-PCR analysis

1: 0-2 mm anther -RT    2: 0-2 mm anther +RT
3: 2-4 mm anther -RT    4: 2-4 mm anther +RT
5: 4-6 mm anther -RT    6: 4-6 mm anther +RT
7: barnase anther -RT   8: barnase anther +RT
9: <microspore -RT      10: <microspore +RT Lanes 1-8: polyA+ mRNA material used
Lanes 9 + 10: total RNA used A) SENSE MAC2 PROBE
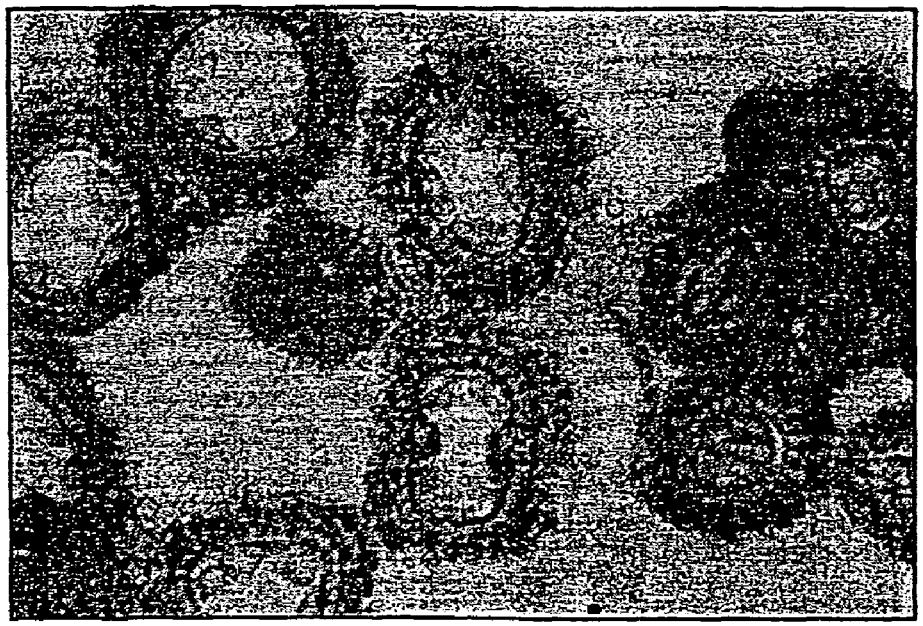
B) ANTISENSE MAC2 PROBE
FIG. 2

Mac2 cDNA sequence.
The putative signal peptide is shown in lower case.

FIG. 3(I)

```
                                                                    Mac2t1
GAGGCATCGCCAAGCAAGTGGAGTAGTACGATGGTGATCAATAGGCCGCAGTTAGTTTCTAGTATAATAGTCTGTTTT       78
                      m  v  i  n  r  p  q  l  v  s  s  i  i  v  c  f

<ACCTGCTGTTTTGCACCTCCAC
GCAAACCTGCTGTTTTGCACCTCCACCGCCTATCCACCACATGTATGTTGACATCACTCAGACTTACAATAGTTTA      156
 a  t  c  c  f  a  P  P  P  P  I  H  H  M  Y  V  D  I  T  T  Q  T  Y  N  S  L

Mac2t2 <CCAAGAGGTCATGCAAAGATACG
TATATTGAGTTTGCAAATCTGCTCAAGATCCCGATAGGGCCTGTATATGATCCCCAAGAGGTCATGCAAAGATACGTT      234
 Y  I  E  F  A  N  L  L  K  I  P  I  G  P  V  Y  D  P  Q  E  V  M  Q  R  Y  V

CTCGGACCTCGCCCGCTTTGGTTTTTATGATGAGCCACCTGAATGGATATATATTCATGTCGTCGGGGAAGAACAAGAC      312
 L  G  P  R  R  F  G  F  Y  D  E  P  P  E  W  I  Y  I  H  V  V  G  E  E  Q  D

Mac2t1 <CTGGCCATAGCCATTGATGACT
AAGGTAACTCTGGCCATAGCCATTGATGACTTATGTCTTATTGGCTTCAGTAATGCTAGTGACCATTGGTACAAGTTT      390
 K  V  T  L  A  I  A  I  D  D  L  C  L  I  G  F  S  N  A  S  D  H  W  Y  K  F

AATGGACAGTCATCATCGTTCAAAGGTTTGCCGGGAGCCACCGTGCTACCGATCAGACAAAATTATCAAGATTTGATC      468
 N  G  Q  S  S  F  K  G  L  P  G  A  T  V  L  P  I  R  Q  N  Y  Q  D  L  I
```

```
AAAGGACACGCCAACCTTTGAAGGTTCCTCTGGGGAAGAAGTCAGCCATACATGCCACCAAGCAGCTTGCGACGTAT   546
 K  G  H  A  N  L  W  K  V  P  L  G  K  K  S  A  I  H  A  T  K  Q  L  A  T  Y

GACCGAGCCGTCACCCCTGACTCCGAACTCAAGGACGGGCTGGTTCGTGTTGATGATGTGTGAAGGCATGCGG       624
 D  R  A  V  T  P  D  S  E  L  K  D  G  L  V  R  F  V  V  M  M  C  E  G  M  R

TTCCGATCGATCCGGACATGTTCTCATCGTTGTCGGCAATAACTGGGAGGAGGAGACCTTCATCACTGAGCTCCAA    702
 F  R  S  I  R  D  M  F  S  S  L  S  G  N  N  W  E  E  E  T  F  I  T  E  L  Q

GCAAAATCTGTCGTCTACTGGTCACAACTCTCGATGCTACTCATTCGTTGGGAGCTAACCGGAAGGCTGCCCGGGGGG 780
 A  K  S  V  V  Y  W  S  Q  L  S  M  L  L  I  R  W  E  L  T  G  R  L  P  G  G

CCAAAATGGGGTGCTGTTGATGGTCGATATAACAGTATGGCTAAGCATGTCCAAGAGGCTATTAATGTCAATGATGCG 858
 P  K  W  G  A  V  D  G  R  Y  N  S  M  A  K  H  V  Q  E  A  I  N  V  N  D  A

AACGATGCTTTGACAATCATTGATTTTCTGCTTCGCCCAACAGAGGAAGTAGATACTGGTAATTAGTTTTAATATATA 936
 N  D  A  L  T  I  I  D  F  L  L  R  P  T  E  E  V  D  T  G  N  *

TAATTATTAGTTACGTCATCGATCTGTGTTGTAAATATTTTATATATACCCTCTAATATTAAAAAAGTAAAATTTCAGCCTT 1014

GTTTCCAAAAAAAAAAAAAAAAAAAAAAAAAAAAAAA                                          1050
```

FIG. 3(II)

Homology scores from Clustal Alignment

```
maize Mac2       297 Amino acids
maize RIP3       300 Amino acids
barley rip1      281 Amino acids
wheat tritin     275 Amino acids Pairwise alignments...

Aligning maize Mac2 with :
       maize RIP3         Score: 14.1414
       barley rip1        Score: 11.3879
       wheat tritin       Score: 11.2727

Aligning maize RIP3 with :
       barley rip1        Score: 17.0819
       wheat tritin       Score: 16

Aligning barley rip1 with :
       wheat tritin       Score: 87.2727
```

FIG. 4(III)

Mac20 RT-PCR analysis

1: 0-2 mm anther -RT
2: 0-2 mm anther +RT
3: 2-4 mm anther -RT
4: 2-4 mm anther +RT
5: 4-6 mm anther -RT
6: 4-6 mm anther +RT
7: barnase anther -RT
8: barnase anther +RT
9: <microspore -RT
10: <microspore +RT Lanes 1-8: polyA+ mRNA material used
Lanes 9 + 10: total RNA used

Mac20 cDNA sequence.
The putative signal peptide is shown in lower case.

FIG. 6

```
GCTTCCAAACTAGAACAACACAATCCAAGAGCGCGTGGGAGAGCGAGCGAAAAAGCAAGATCAAGAGAGAGCGATCGA    78

GAGAAGACAACACAAGAAGCAATAAAGAGTCGGGAGCCGAAGGACCGATGGCCGTCTACTTCAGCATCACCGC       156
                                       m  a  v  y  f  s  i  t  a

CTTCCTTGTCGTCATCATCCTGGTCCGCGTGCGGCGTCGTTTTGTCAATGTCGTCATCATCTGGGGCTTT          234
 f  l  v  v  i  i  l  v  l  a  a  c  g  v  v  f  v  n  v  v  i  i  w  g  f

CGCCCTCGCCGCGTCCGTTCTCGTTCTTACTGTCCAAGGTCAAGTGGCATTCGGCGCTACCGCCATCGTCACGGAT     312
 a  l  a  A  S  P  F  F  S  F  L  L  S  K  V  K  W  H  S  R  L  P  P  S  R  M

GCCGGAGGAGGAGTTGATGTTTCCGTGCCACTGGTTCGACGAAACACTACTGCAGGCGGACTCGGAGGAGGAGGTGCT   390
 P  E  E  E  L  M  F  P  P  S  H  W  F  D  E  T  L  L  Q  A  D  S  E  E  E  V  L

GCTTCCGACGCACTGGTTCGACGAAACACTATTGCAGGAGTCTACATCGTAGTAGACAGCCGTGATCGAGCTTGGATG   468
 L  P  T  H  W  F  D  E  T  L  L  Q  E  S  T  S  .  .

GGACGGAGTTGACGCGTCCTTTGGAACTGGATCAGTTCTTGTTCTTGAAGTTGAAGGATTCTTTCGACGTTTCTGTCA   546

CTGCATTTTTGGAACTGATCAAGGGTACTGGTGTGCCGTGGTGCCGTGGTGCCGTGATCAGTCTAGATTAGTTATTGAAACATTTT   624

TTCATTGTTTCTGCCATTCGCTTTCTGAAACTATCGAGCTTAGCTGCGTTCATGCTCTTTTGTTCAGATTCGTGTT     712

CAGCTGCCGACGAACTGAATTTCTTGATGCCAAGAAACGATGGTTTGTTAGTCCTTGGATCAGTTAGAGTGTTCTGACT  780

GAAGCAAAAGATCCTTGGTTCATTGCTCTTTCCAAAAAAAAAAAAAAAAAAAAAAAA                        839
```

FIG. 7(I)

```
                     SalI
ntcgastwtsgwgtt> AD1    ggtcgacttggaataatttaagttgt> NewMac2P5'
GTCGAGTAGTGGAGTTCGAACCCGTGTATACAAGTGATGCACTTGGAATAATTTAAGTTGTGTGGAAATGATG    70
                  T
AATTTATTATTATCGAGGTAGCATAATTTAAAAATTGGAACTGTTGAAGGCTAAGTATATTTTTGTTCCCAAT  140
                     C
ATATATTTATGAACTTGCTAAATTAAAGTTTATGGAGCTTTTTTTTTGAAGTAATGGAGATGCTCTAAAG     210
GGAGGTCATTTGCAAACAAATTTAAGAATAAAAAGGAAAACACAGGAGCAGCTATAGGTAAGGTGCTA       280
                                                A
TAATCGAAAAAGAATTGTTGTACTAGTAGTAGCATTCGAGGAGCATTTGTAGCTAGATGATTAAGGTAAAA    350
AAAAGTGTGACTGCTGCGGGCCAAAGAAGCATGCGCAAATCTTTCTCTCGGCTCCCTTTGCATGCACAACC   420
TACTCAGTCTTTAGAAAAATAAAGTTTTCAAACTAGTCCTTAGGGTGGAATTGATTCTAGCGTTTGGTTA    490
                            A
CGGAGGCCCATCTCCATTAGTCTTCCCGAAAAAGAAGTTCCTAAAATTAATTTAGGGTGTTAATAACAAAAAA 560
                                            A
AAATAATGCTCCAACAATTTCTTGAATAAGATTATCAAATATACTAAAATATATATCTCTATTAATGTATT   630
```

```
                                                                       A
CTCTAAACTTGGGGAGTTGTTTCGTATGCCCAATGACCTATTCTGCTCATAAATCGTACCGTGAAATAAT  700
                       A
                                          A           C
TACTTGTCAGCCATATGAGTTCGCACCGTGTATACAAGTGATGCACTTAGAATGATTTAAGTTGCGGAAA  770
                                          A
                                                      A

TGATGAATTTATTATCGAGGTAGCATAATTTAAAAACTGGAACTGTTGGAGGTTAAGTATATTTTGTTC  840

CTAAATATATATTTATGAACTTGCTAAATTAAAGTTTGTGGAGCTTTTTTTTTGAAGTAATGGAGATGCT  910

CTAAGGGGAGGTCATTTCTAAACAAATTTAAGAATAAAAAAGGAAAACACAGGAGCAGCTATAGGTAAG  980

GTGCTATAATCGAAAAATAATTGTTGTACTAGGTAGCATTCGAGGAGCATTTGTAGCTAGATGATTAAG  1050

GTAAAAAAGTGTGACTGCTGCGGGCCAAAGAAGCATGCGCAAATCTTTCTCTCGGCTCCCCTTTGCATGCA  1120

CAACCTACTCGCTACCTTACCCCGCTCGATCTGTGCATGCACAGGTATATATATATACC  1190
                                                    NcoI
                                  Mac2P3'N <gtggagtagtaccatggtgatc
TAGCTAGCTGCTAGTTTGTCGTCCCAGCCCAGGCATCGCCAAGCAAGTGGAGTAGTACGATGGTGATCAA  1260
                                                     M  V  I  N
                 Mac2t3 <acctgctgtttgcacctccac
TAGGCCGCAGTTAGTTGTAGTATAATAGTCTGTTTTGCAACTGCTGTTTTGCACCTCCAC>  1320
 R  P  Q  L  V  C  S  I  I  V  C  F  A  T  A  V  L  H  L  H
```

FIG. 7(II)

PARTS B-D

PARTS B-E

```
GAGGCATCGCCAAGCAAGTGGAGTAGTACGATGGTGATCAATAGGCCGCAGTTAGTTTCTAGTATAATAGTCTGTTTT        78
                                  m  v  i  n  r  p  q  l  v  s  s  i  v  c  f
         NcoI
         cc catg gcctccaccgcgcctatcc>  ΔMac2F
GCAACCTGCTGTTTTGCACCTCCACCGCCTATCCACCACATGTATGTTGACATCACTACTCAGACTTACAATAGTTT/       156
 a  t  c  c  f  a  P  P  P  P  I  H  H  M  Y  V  D  I  T  T  Q  T  Y  N  S  L
                           .
                           .
                           .
/CAAAATGGGGTGCTGTTGATGGTCGATATAACAGTATGGCTAAGCATGTCCAAGAGGCTATTAATGTCAATGATGCG       858
  P  K  W  G  A  V  D  G  R  Y  N  S  M  A  K  H  V  Q  E  A  I  N  V  N  D  A
                                                          SstII
                                      ΔMac2R  <ggaagtagatactggtaattaccgcggc
AACGATGCTTTGACAATCATTGATTTTCTGCTTCGCCCAACAGAGGAAGTAGATACTGGTAATAGTTTTAATATATA        936
 N  D  A  L  T  I  I  D  F  L  L  R  P  T  E  E  V  D  T  G  N  •

TAATTATTAGTTACGTCATCGATCTGTGTAATAGTTTATATATACCTCTAATATTAAAAAAGTAAAATTTCAGCCCTT      1014

GTTTCCAAAAAAAAAAAAAAAAAAAAAAAAAAAAAA                                              1050
```

Sequence of Mac20 genomic fragment, including 585 bp of upstream region and the proposed Mac20 coding region.

```
TACGGGACCCATATTTCTACAGGCGGGCCCTGCTAGTATACACTATGTCTAGAGATGTATAGTTGGGTTTAATTTGCATTT      78
TGTCGGGTTAATTTGCATTTTATAATTTAGAACGGAAGGAGTAGCATTTGTCAGTTTAATTTCATTTCTTTGTGT         156
TAGTTGGGTGCCCACGCCATCCAACTCTTCAAGAAGCTCTTTAGTTGTTAGGGACACTGGTACTGTCTGAAACATCGAA      234
CTATCTATAAGATTTCATTTCACAAACAAAACTGGGAGTCTCCATTCCAACCATCCTGCTCTTTCCATTTTCATCC        312
GGTCATCCCCCTCGCCCCTCCCCAGTTTCAAGTTTGAACCGTGCGCCCTTTGGGAATCGAGCCCGTGGGTCCCA          390
CCTTGTAAAGAACTGATCAAGCCAATGACTTATCAACATCCTCGCTACAAATATCCGCCACCCTAATTTGGCCAAGC       468
CTTCCAAACGAAGAACAACAATCAAGAGCGACGTGGGAGCGAGCGAGAAAGCAAGATCGAGAGAAGAGACAC            546
```

```
AAGAAGCAATAAAGAGTCGGGACCGGAGTGAAGGACCGATGGCCGTCTACTTCAGCATCACCGCCTTCCTTGTCGTC  624
                         M  A  V  Y  F  S  I  T  A  F  L  V  V

ATCATCCTGGTCCTGGCCGCGGTGCGCGGGTCGTTTTGTCAATGTCGTCATCATATGGGCGTTCGCCCTCGCCGCG  702
 I  I  L  V  L  A  A  C  G  V  V  F  V  N  V  V  I  I  W  G  F  A  L  A  A

TCTCCGTTCTCGTTCTTACTGTCCAAGGTCAAGTGGCATTCGCGGCCACCGCCATCGTCACGGACGTCGGAGGAGGAG  780
 S  P  F  S  F  L  L  S  K  V  K  W  H  S  R  P  P  P  S  S  R  T  S  E  E  E

TTGATGTTTCCATCGCACTGTTCGACGAAACACTATTGCAGGAGTCTCCATCGCAGTAGCAGGCGTGATCGAGCTTGAC  858
 L  M  F  P  S  H  W  F  D  E  T  L  L  Q  E  S  P  S  Q  *

TGGTTCGACGAAACACTATTGCAGGAGTCTCCATCGCAGTAGCAGGCGTGATCGAGCTTGACGTGACGGAGTTGAC  936
 W  F  D  E  T  L  L  Q  E  S  P  S  Q  *

GCGTCCTTTGGGGCGGTCTCGATCAGTTCTTGTTCTAGAAGTTGAATGATTCTTTCGACGTTTCTGTCACTGCATTT 1014

TTGAACTGATCAAGGTAGTATGCTGGTGCCGTGTCGCCTGATAGTCTAGATTAGTCATTGAAACATTTTTCCATTGT 1092

TTCTGCCATTCGCTTTCTCTTGGAAACTATCGAGCTTAGCTGC                                  1133
```

FIG. 12(II)

TAPETUM-SPECIFIC PROMOTERS

CROSS REFERENCE TO RELATED APPLICATIONS

The present application is the National Phase of International Application No. PCT/GB00/01789, filed May 10, 2000, which was published in English, and claims priority to Great Britain Appl. No. 9910796.3, filed May 10, 1999, the disclosure of which is incorporated in its entirety by reference hereto.

BACKGROUND OF THE INVENTION

Field of the Invention

This invention relates to the application of recombinant DNA technology to plants, for the purpose of achieving male sterility.

This invention relates to the application of recombinant DNA technology to plants, for the purpose of achieving male sterility. The production of hybrids via sexual hybridisation of parents with differing genetic backgrounds is an important practice in modern agriculture. Due to the manifestation of hybrid vigour the offspring are superior to the parents in such characters as yield and disease resistance. In addition, where the parents are extensively homozygous, the resulting offspring are genetically very uniform, and therefore the crop behaves in an equally uniform manner in such important characteristics as germination time, height of growth, susceptibility to disease, flowering time, seed ripening time etc, which greatly improves the efficiency of crop management. For these reasons hybrid seed is attractive to the farmer.

In nature, self-fertilisation is favoured with the production of non-hybrid offspring. Therefore, in order to produce hybrid seed free from contamination with selfed seed, cross-fertilisation is carried out using a variety of mechanical, chemical and genetic methods that prevent self-pollination. This can be achieved in a number of different ways:

(a) by mechanically removing or chemically inactivating the pollen-producing organs of the female parent before they reach maturity; this method has been used for example in maize (corn) and tomato;

(b) by using cytoplasmic male sterile (CMS) mutant plants; this method has been used for example in oilseed rape and sunflower, (c) by using a recessive nuclear male sterile mutant plant; and (d) by using a dominant nuclear male sterile genetically engineered plant (artificial male sterility or AMS) as described for example in Mariani et al, Nature 347 737–741 (1990) or in Worrall et al, The Plant Cell 4 759–771 (1992).

There are practical difficulties with all of the above. Mechanical male sterilisation is labour intensive, costly and prone to human error, giving a problem of the quality of hybrid seeds. It is practical only for the species where the flower is big enough to be emasculated manually; it is not practical therefore for most cereals. An attempt to overcome this difficulty and reduce costs uses chemical instead of mechanical emasculation. The efficiency of this technique is very dependent on environmental conditions at the time of spraying the gametocide, and leads the seed producer to take a considerable risk each season.

Cytoplasmic male sterility is very convenient, but its use is limited by the availability of the appropriate mutant plant in each species of interest. The loss of cytoplasmic genetic diversity when all breeders use the same cytoplasm in their breeding program can be a serious problem as seen in the US in maize in the 1970's.

The use of recessive nuclear male sterile mutants is not practical. Because the male sterility gene is recessive, maintenance of the male sterile line involves screening the ¼ of male plants out of the ¾ fertile in the selfed progeny of an heterozygous plant. In the absence of a tightly linked selectable or easily screenable marker this is practically impossible.

The use of AMS systems provides a means of avoiding the problems associated with the other methods. AMS gene systems are potentially universal, being limited only to genetically transformable species. It does not rely on the existence of a mutant as in CMS. The maintenance of the male sterile line may be obtained by engineering a dominant male sterility gene linked to a marker gene that allows selection of AMS plants in a population segregating ½ AMS plants. To be practical, this marker is often a herbicide resistance gene.

AMS systems generally make use of tissue specific expression, for instance by utilising promoters/regulatory sequences which drive expression in one or more of those tissues involved in the development of male fertility. For example, the tapetum, which is a specialised cell layer within the anther and which plays a crucial role in the supply of nutrients to the developing microspores. Malfunction of the tapetum is the cause of many types of natural male sterility.

Certain tapetum-specific genes and their promoters have been previously isolated from both dicots and monocots. For example, WO 92/11379 discloses pA3 and pA9, which probably represent the earliest expressed tapetum-specific promoters isolated to date. Monocot genes which are A9-like have also been disclosed. These are sequences whose coding regions, when translated, putatively encode a protein with homology to A9. Examples of these include the Maize promoter Msfl4 (Wright S Y, et al., Plant J. 1993 (1): 41–9.), which is almost identical to, and is therefore probably the same as Ca444 (WO 92/13957); Osg4 from rice (Tsuchiya et al, Plant Mol. Biol., 26(6):1737–46); and LH6 and LH7 from lily. In addition, there are several monocot tapetum-specific cDNAs or promoters isolated from monocots that are not A9-like. These are Ca455 and its promoter pa55 from maize (WO 92/13957); pE1 and pT72 from rice (WO 92/13956); and pOSG6B from rice (Tsuchiya et al, supra).

There is no evidence that any of these promoters can form the basis of an efficient AMS system in monocots, utilising a preferred AMS sterility gene such as PR-glucanase. Moreover, certain promoters such as pA3 and pA9, although efficient in certain dicots such as tomato (WO97/38116), when linked to PR-glucanase only produce a low frequency of complete male sterility in other dicots such as tobacco (Worrall et al, The Plant Cell, 4:759–771 (1992)). We have now identified additional promoters that are more efficient in generating male sterile monocot and dicot plants using a preferred sterility gene such as PR-glucanase, than other promoters previously described.

Thus, in a first aspect, the present invention provides a recombinant or isolated nucleic acid molecule comprising or consisting of a promoter which is:

(i) the pMAC2 promoter sequence as shown in FIG. 7 (SEQ ID NO:19);

(ii) the pMAC20 promoter sequence as shown in FIG. 12 (SEQ ID NO:28);

(iii) a promoter controlling expression of a coding sequence which is substantially homologous to those shown in FIG. 3 (SEQ ID NO:9) or FIG. 6 (SEQ ID NO:17); or (iv) a sequence capable of hybridizing under stringent conditions to any one of (i), (ii) or (iii).

Such promoters are tapetum specific. That is to say, that in the context of the present invention these promoters primarily drive expression in the tapetum.

In the context of the present invention the term "substantially homologous" means that said sequence has a greater degree of homology with any of the sequences described herein than with prior art nucleic acid sequences.

When comparing nucleic acid sequences for the purposes of determining the degree of homology one can use programs such as BESTFIT and GAP (from the Wisconsin Package™, Genetics Computer Group (GCG) Madison, Wis. USA). BESTFIT, for example, compares two sequences and produces an optimal alignment of the most similar segments using the algorithm of Smith and Waterman (Advances in Applied Mathematics 2: 482–489, 1981). GAP enables sequences to be aligned along their whole length and finds the optimal alignment by inserting spaces in either sequence as appropriate, using the algorithm of Needleman and Wunsch (J. Mol. Biol. 48: 443–453, 1970). Suitably, in the context of the present invention when discussing homology of nucleic acid sequences, the comparison is made by alignment of the sequences along their whole length.

Preferably, sequences which have substantial homology have at least 50% sequence homology, desirably at least 75% sequence homology and more desirably at least 90 or at least 95% sequence homology with said sequences. In some cases the sequence homology may be 99% or above.

The skilled person will appreciate that what is important is that any sequence functions as a promoter and will drive expression primarily in the tapetum.

In the context of the present invention, suitable "stringent conditions" are defined as those given in Plant Genetic Transformation and Gene Expression: A laboratory manual, Ed. Draper, J. et al, 1988, Blackwell Scientific Publications, pp252–255, modified as follows: prehybridization, hybridization and washes at 55–65° C., final washes (with 0.5× SSC, 0.1% SDS) omitted.

In addition, it is possible to derive essential regulatory elements from the promoters provided herein. Thus, those elements of the promoter sequence responsible for both its function as a promoter and, more importantly, its tapetum specificity, can be isolated and incorporated into nucleic acid molecules which, although not falling within the definitions (i) to (iv) above, nonetheless still function in an equivalent manner.

Therefore, in a second aspect, the present invention provides a recombinant or isolated nucleic acid molecule comprising or consisting of one or more regulatory elements derived from any one of the sequences (i) to (iv) capable of driving expression in a tapetum specific manner.

In addition, the pMac2 putative protein possesses a signal peptide which targets the protein for secretion in the endoplasmic reticulum (see example 5), preventing access of MAC2 to the tapetal cell ribosomes. Removal of the signal peptide allows the Mac 2 protein to accumulate in the cytosol and inactivate the ribosomes causing cell death. Thus, a MAC2 protein lacking a signal peptide can be used as a cellular ablator. Thus, in a further aspect, the present invention provides a recombinant or isolated nucleic acid molecule encoding a MAC2 protein lacking its natural signal peptide.

Such a nucleic acid can be obtained by means of PCR amplification of sequence shown in FIG. 3 (SEQ ID NO:9) using suitable primers having the sequence:

5' CCCATGGCCTCCACCGCCTATCC 3' (SEQ ID NO:1)

5' GCCGCGGTAATTACCAGTATCTACTTCC 3' (SEQ ID NO:2)

or a sequence which hybridises thereto under stringent conditions. Such primers form an additional aspect of the invention.

Suitably, the nucleic acid molecule in the above-noted aspects of the invention is a DNA molecule.

The tapetum specific promoters of the invention find use in AMS systems. Thus, they may be used to drive the expression of a variety of sterility DNA sequences which code for RNAs proteins or polypeptides which bring about the failure of mechanisms to produce viable male gametes. A number of classes and particular examples of male-sterility sequences are preferred.

For example, the male sterility DNA may encode a lytic enzyme. The lytic enzyme may cause lysis of one or more biologically important molecules such as macromolecules including nucleic acid, protein (or glycoprotein), carbohydrate and in some circumstances lipid.

Ribonuclease (such as Rnase T1) and barnase are examples of enzymes which cause lysis of RNA. Glucanase is an example of an enzyme which causes lysis of a carbohydrate. The enzyme callase (a β(1,3)-glucanase) is naturally produced in anthers where it functions to release the young microspores from a protective coat of poly-glucan (callose) laid down before meiosis. The appearance of the enzyme activity is developmentally regulated to coincide with the correct stage of microspore development.

One advantage of using glucanase as a male sterility DNA is that it is less prone to potential problems of ectopic expression. In certain environmental conditions or at a particular developmental stage it is possible that transgenes will be expressed at low levels ectopically. This expression may be due to the activation of genes and promoters surrounding the transgene or the expression of transactivators that bind in the vicinity of the transgene (position effect). It is not predictable whether a particular transgene will be ectopically activated in a given environmental condition or developmental stage given that the genomic sequence surrounding each transgene may be unique. This is since current transformation technologies result in an unpredictable integration of the transgene into the genome. Such problems of unpredictable transgene expression are particularly serious with highly active non cell-specific cytotoxic transgenes such as barnase. It has been claimed that a single barnase protein is sufficient to cause cell death. Extensive field trialling of barnase transformants will eliminate the majority of transformations where such ectopic expression occurs. However this is laborious and there is always a chance that conditions that cause ectopic expression are not encountered prior to commercialisation of the plant line.

Such a problem of ecotopic barnase expression can minimised by 'constitutive' expression of the inhibitor of barnase, barstar such that it is expressed in all cell types apart from the target cell type (eg the anther tapetum). However constitutive expression of barstar may be undesirable since all plant parts consumed now contain barstar protein. Also, not all cell types may have sufficient expression of barstar to be protected.

Glucanase and barnase represent preferred embodiments of a lytic enzyme for use with the nucleic acid molecules of the invention.

A further advantage is that the PR glucanase system is more 'natural' than the barnase system. Premature expression of PR-glucanase mimics or phenocopies natural male sterile sorghum and petunia mutants (Worrall et al., (1992) Plant Cell. 4, 759–771).

Male sterility DNA does not have to encode a lytic enzyme. Other examples of male sterility DNA encode enzymes which catalyse the synthesis of phytohormones, such as isopentyl tranferase, which is involved in cytokinin synthesis, and one or more of the enzymes involved in the synthesis of auxin. A further example of a male sterility DNA encodes an RNA enzyme (known as a ribozyme) capable of highly specific cleavage against a given target sequence (Haseloff and Gerlach, Nature 334 585–591 (1988)).

Other male sterility DNAs include antisense sequences. Introducing the coding region of a gene in the reverse orientation to that found in nature can result in the down-regulation of the gene and hence the production of less or indeed none of the gene product. The RNA transcribed from antisense DNA is capable of binding to, and destroying the function of, a sense RNA version of the sequence normally found in the cell, thereby disrupting function.

It is not crucial for antisense DNA to be solely transcribed at the time when the natural sense transcript is being produced. Antisense RNA will in general only bind when its sense complementary strand is present, so will only have its toxic effect when the sense strand is transcribed.

In a further aspect, the present invention provides a set of primers suitable for PCR amplification of the promoter region of the maize MAC2 gene and having the following sequence:

3' GGTCGACTTGGAATAATTTAAGTTGT 5' (SEQ ID NO:3)

3' GATCACCATGGTACTACTCCAC 5' (SEQ ID NO:4)

or having a sequence which hybridises thereto under stringent conditions.

The primers used may be used to amplify a promoter from maize genomic DNA. A person skilled in the art will appreciate though that the same primers may be suitable for PCR amplification from other monocots such as rice, wheat and lily.

DNA in accordance with the invention may be in the form of a vector. Such vectors form an additional aspect of the invention. The vector may be, for example, a plasmid, cosmid or phage. Vectors will frequently include one or more selectable markers to enable selection of cells transfected or transformed and to enable the selection of cells harbouring vectors incorporating heterologous DNA. Examples of such a marker gene include antibiotic resistance genes (EP-A-0242246) and glucuronidase (GUS) expression genes (EP-A-0344029). Expression of the marker gene is preferably controlled by a second promoter which allows expression in cells other than the tapetum, thus allowing selection of cells or tissue containing the marker at any stage of regeneration of the plant. The preferred second promoter is derived from the gene which encodes the 35S subunit of Cauliflower Mosiac Virus (CaMV) coat protein. However, any other suitable second promoter could be used.

Cloning vectors may be introduced into *E. Coli* or another suitable host which facilitate their manipulation. Nucleic acid sequences in accordance with the invention may be introduced into plant cells by any suitable means. Thus, according to yet a further aspect of the invention, there is provided a plant cell including a nucleic acid molecule in accordance with the invention. Preferably, the plant cell with be transgenic.

Nucleic acid may be transformed into plant cells using a disarmed Ti-plasmid vector and carried by *agrobacterium* by procedures known in the art, for example as described in EP-A0117618 and EP-A-0270822. Alternatively the foreign nucleic acid could be introduced directly into plant cells using a particle gun. This method may be preferred for example when the recipient plant is a monocot.

A whole plant can be regenerated from a single transformed plant cell. Thus, in a further aspect the present invention provides transgenic plants (or parts of them, such as propagating material, which may also be transgenic) including nucleic acid sequences in accordance with the invention. The regeneration can proceed by known methods. When the transformed plant flowers it can be seen to be male sterile by the inability to produce viable pollen. Where pollen is produced it can be confirmed to be non-viable by the inability to effect seed set on a recipient plant.

In final aspects, the present invention provides:

(a) the use of the nucleic acid molecules of the invention in transforming a host cell, preferably a plant cell, and more preferably a monocot plant cell; and (b) the use of the nucleic acid molecules of the invention in the production of a male sterile plant.

Preferred features for each aspect are as for each other aspect *mutatis mutandis*.

The invention will now be described by the way of the following examples, which should not be construed as in any way limiting the scope of the invention. The examples refer to the accompanying drawings.

BRIEF DESCRIPTION OF THE DRAWINGS

FIG. 2—shows the in situ data for Mac2. Sections of a male floret were probed with labelled sense Mac2 as a control (A) or with labelled antisense Mac2 (B). The tapetum can been seen to be heavily labelled (black circles) only with the sense probe.

FIG. 3—shows the Mac2 cDNA sequence (SEQ ID NO:9). The predicted amino acid sequence of the Mac2 protein (SEQ ID NO:10) is shown underneath the DNA sequence. Primers used for TAIL-PCR are shown above the cDNA sequence (SEQ ID NO:11; SEQ ID NO:12; SEQ ID NO:13).

FIG. 6—shows the Mac20 cDNA sequence (SEQ ID NO:17). The predicted amino acid sequence of the Mac20 protein (SEQ ID NO:18) is shown underneath the DNA sequence.

FIG. 7—shows the TAIL-PCR sequence of Mac2T-3 (SEQ ID NO:19). The AD1 (SEQ ID NO:8) and Mac2t3 (SEQ ID NO:11) primers used to PCR this sequence are shown above the DNA sequence. Nucleotide differences compared to Mac2T-1 and other TAIL-PCR products are shown beneath the DNA sequence ('-'=missing nucleotide). The amino acid sequence of the putative Mac2 peptide (SEQ ID NO:20) is shown underneath the DNA sequence. The sequences of primers used to PCR the promoter (SEQ ID NO:21; SEQ ID NO:22) are shown in lower case above the TAIL-PCR sequence. Two sequence changes in the PCR product compared to the TAIL-PCR sequences are indicated above the TAIL-PCR sequence.

FIG. 9B shows a single pollen sac from a wild type plant; FIG. 9C shows a single pollen sac from a plant carrying the Mac2-barnase construct; and FIG. 9D shows a low magnification view of anther section from a Mac2-barnase plant in which all four pollen sacs are visibly collapsed.

FIGS. 10B and 10C show fluorescence micrographs of wild type and transformed tobacco microspore tetrads respectively, stained for callose with aniline blue. FIGS. 10D and E show scanning electron micrographs of tobacco microspores/pollen from a wild type and transformed plants, respectively.

FIG. 12—shows the pMac20 genomic sequence (SEQ ID NO:28) with the putative Mac20 peptide sequence (SEQ ID NO:29) shown below the DNA sequence.

EXAMPLE 1

Figure 1:
FIG. 1—shows the RT-PCR data for Mac2. The maize RNA source used in each reaction is indicated below the gel. –RT reactions are control reactions lacking reverse transcriptase. +RT reactions contain reverse transcriptase. 1 kb Ladder (Gibco BRL) is loaded as a DNA size marker either side of lanes containing RT-PCR products.

Isolation of Maize cDNAs Representing Transcripts of Tapetum-Specific Genes Expressed Prior to Microspore Release In Most Plant Species the Stage of Microsporogenesis within Anthers is Strongly correlated with the length of floral buds and anthers (Scott et al. (1991) Plant Mol Biol. 17, 195–207). Microscopic analysis of anthers from the maize variety A188 established the following correlation between anther length and developmental stage:—0–2 mm=prior to tetrad stage. 2–4 mm=tetrads, microspore release and free microspores. 4–6 mm=free microspores.

In order to utilise a male sterility system based on the premature degradation of callose (β(1,3)-linked glucan) formed in meiosis it is necessary to isolate the promoter of a gene that is highly expressed during the developmental phase where callose surrounds the microsporocytes, microsporocytes undergoing meiosis and the tetrads. Thus it is essential that this promoter is expressed prior to microspore release (MR). The promoter should also be expressed in the tapetum and/or microsporocytes. Such promoters are, of course, potentially useful in male sterility systems that are not based on premature callose degradation.

Consequently, 100 mg of anthers containing microsporocytes prior to microspore release (<MR) were dissected from male florets of maize variety A188, and 13 μg of total RNA isolated using a Rneasy Plant Mini Kit (Qiagen) according to manufacturers instructions. 840 ng of total RNA was used to construct a cDNA library in Lambda gt11 using the Capfinder PCR kit (Clonetech) according to manufacturers instructions.

To provide probes to differentially screen this <MR cDNA library, cDNA was prepared from <MR anther, 0–2 mm anther, A9-barnase anther and seedling RNA and labelled with DIG using the DIG-High Prime kit (Boehringer Mannheim). This cDNA was used to screen plaque lifts from the library according to methods provided in the Dig User's Guide supplied by Boehringer Mannheim. First the <MR cDNA library was differentially screened with maize seedling and <MR anther probes. 42 plaques that potentially represented anther-specific messages were rescreened against seedling, anther, and also against A9-Barnase anther probes (transformation of maize with the chimeric gene A9-Barnase (Paul et al., *Plant Molecular Biology* 19 611–622 (1992)) results in male sterile plants due to the ablation of the anther tapetum. Thus if the plaque represents a message expressed in the anther tapetum the hybridisation signal should be absent or reduced. This secondary screening showed that 26 plaques represented messages present in fertile anther RNA but absent in seedling and barnase anther RNA.

The 26 cDNAs were PCRed out from Lambda gt11, recloned into pGEM-T (Promega) and the DNA sequence determined. This analysis showed that the 26 cDNAs comprised of 8 groups. Two primers were designed to each of the 8 groups and RT-PCR used to determine the spatial pattern of expression and confirm the spatial expression of the clones. The RNA used in this analysis was from <MR, A9 barnase, 0–2 mm, 2–4 mm and 4–6 mm anthers. From this screening two clones, Mac2 and Mac20 were selected as being potentially representing strongly expressed tapetum-specific and/or microsporocyte-specific genes expressed prior to microspore release.

i) Mac2

This cDNA was represented 8 times in the 26 cDNAs resulting from secondary screening. RT-PRC data (FIG. 1) shows Mac2 mRNA is abundant in 0–2 mm anthers, is also present at reduced levels in older anthers (2–4 mm) which are largely 'post microspore release' but is absent in older 4–6 mm anthers. Surprisingly Mac2 mRNA is also present in A9-Barnase anthers (FIG. 1, lane 8) in which the tapetum is ablated.

In situ analysis of sectioned anthers was performed performed essentially as described in the Boehringer Manheim Non-Radioactive In Situ Hybridisation Manual. 15 μm and 30 μm sections were cut using a cryostat (Shandon). RNA probes were labelled using the DIG RNA labelling kit (Boehringer Manheim) according to manufacturers instructions and hybridisation was performed overnight at 42° C. Results (FIG. 2) show that Mac2 mRNA is present in the tapetum of maize anthers and is absent in the anther wall. Given that Mac2 is tapetum-specific the finding that Mac2 mRNA is also present in A9-Barnase anthers indicates that in maize the *Arabidopsis thaliana* A9-tapetum-specific promoter is expressed after the appearance of Mac2 mRNA. This suggests that the promoter of Mac2 will be expressed earlier than that of pA9 and thus will be superior for the premature expression of β(1-3) glucanase.

DNA sequence analysis shows that the longest Mac2 cDNA putatively encodes a 297 amino acid protein with a putative signal peptide predicted by the program Signal P (Neilson et al., (1997) Protein engineering 10 1,6) (FIG. 3)

Figure 4I:
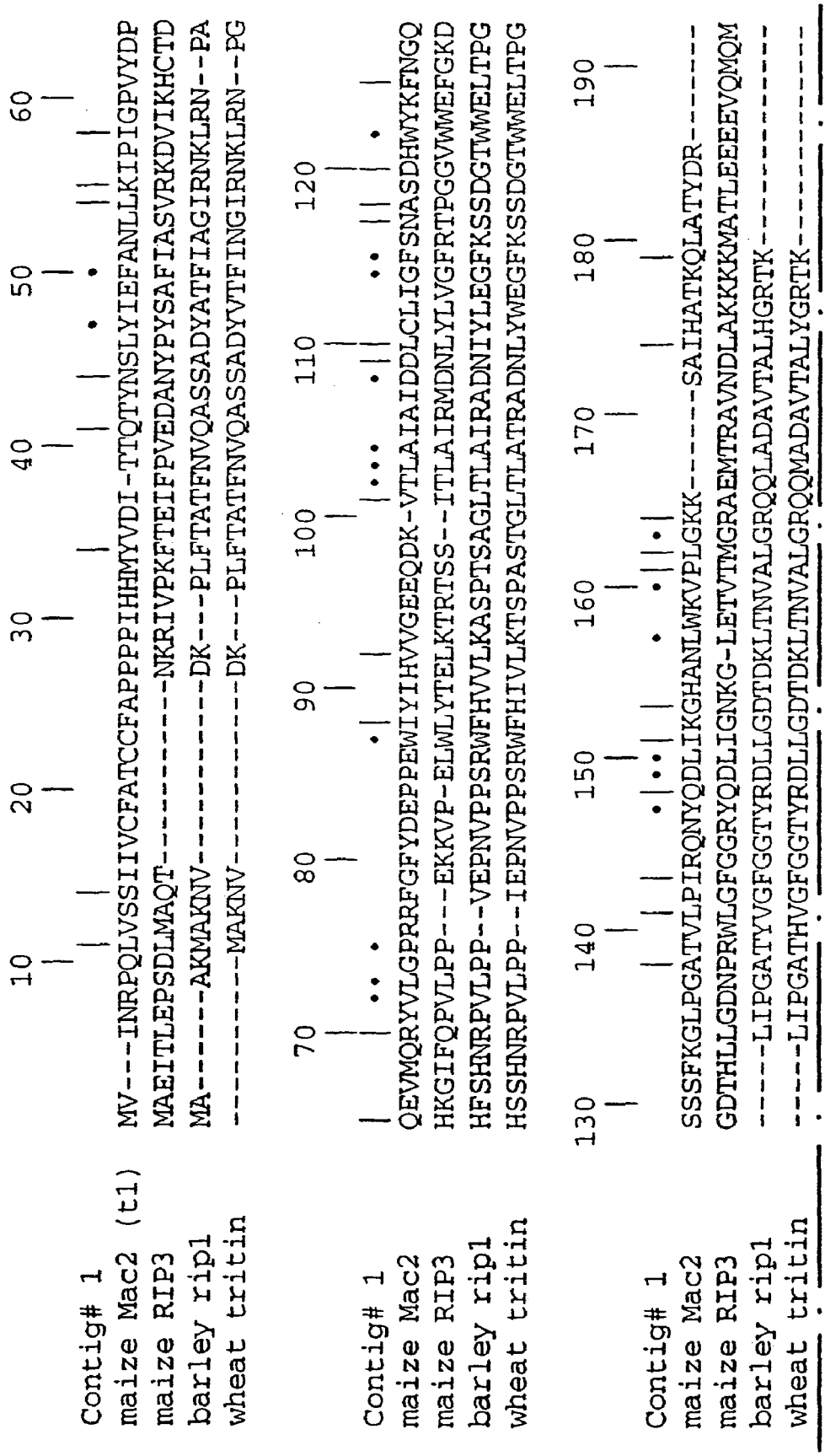
FIG. 4—shows the alignment of Mac2 with type 1-RIPs. Genebank accession numbers for sequences are: Maize RIP3 (M83926)(SEQ ID NO:14), Barley RIP1 (M62905, M36990)(SEQ ID NO:15) and Wheat Tritin (D13795)(SEQ ID NO:16).
Figure 4:
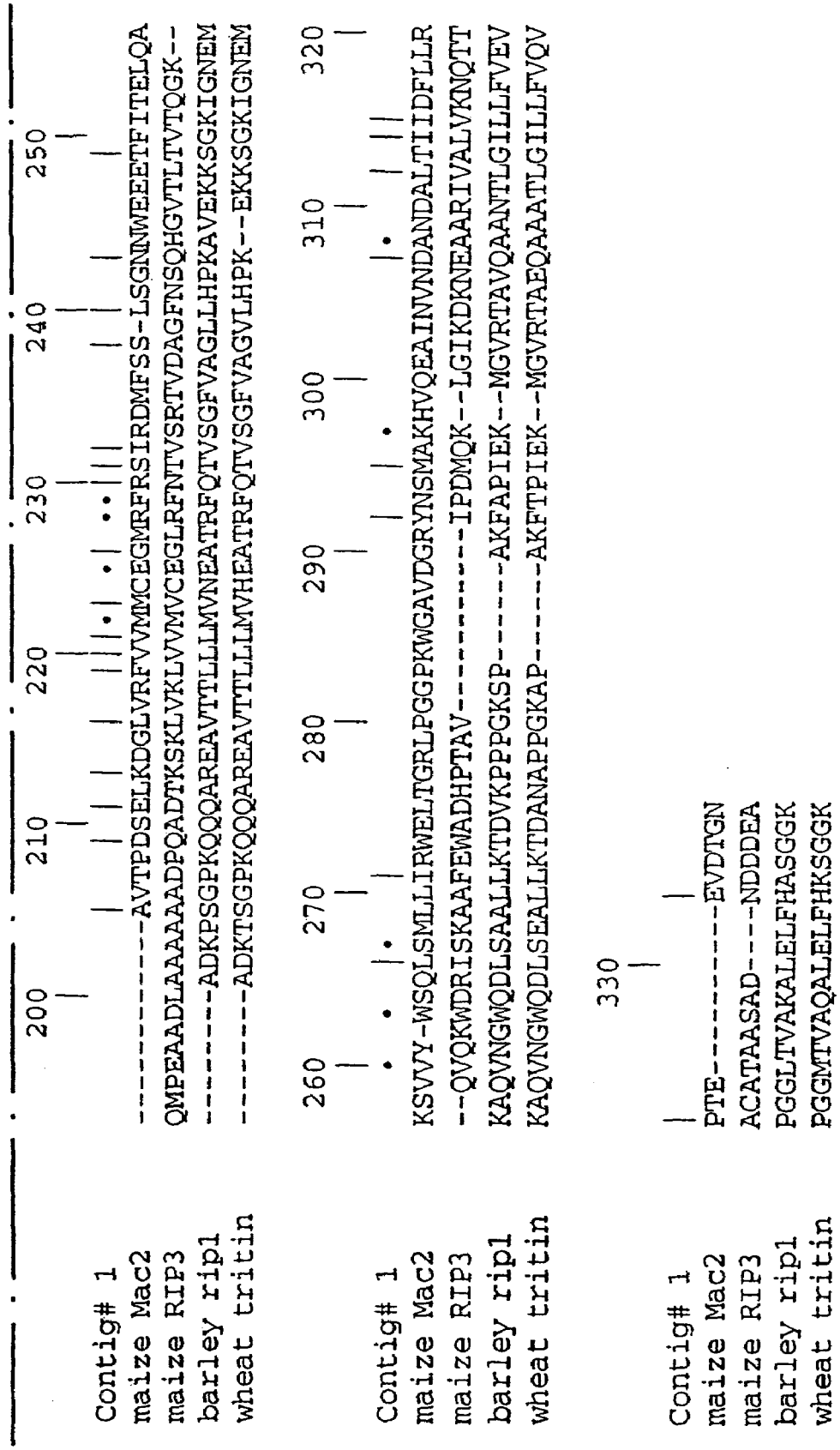

(SEQ ID NO:9). Database searches show that the Mac2 putative protein shows low homology to type 1-ribosome inactivating proteins (RIPs) from maize, wheat and barley that are expressed in seeds (FIG. 4). The best homology is with Maize RIP3 with 17% identity at the protein level (Clustal V score of 14.1). Southern analysis showed that the Mac2 cDNA hybridises to 3 or 4 bands in maize genomic DNA cut with EcoRI. Hybridisation was performed at 65° C. using a Digoxigenin-labelled Mac2 probe as described in Protocols for Nucleic Acid Analysis by Nonradioactive Probes, Methods in Molecular Biology Vol 28 (1994) Ed. Isaac PG Humana Press Inc.

ii) Mac20

Figure 5:
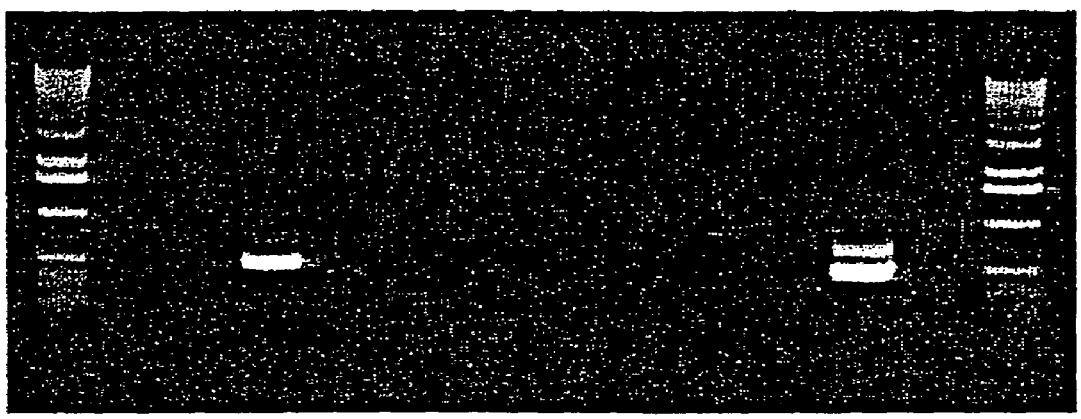
FIG. 5—shows the RT-PCR data for Mac20. The maize RNA source used in each reaction is indicated below the gel. –RT reactions are control reactions lacking reverse transcriptase. +RT reactions contain reverse transcriptase. 1 kb Ladder (Gibco BRL) is loaded as a DNA size marker either side of lanes containing RT-PCR products.

This cDNA was represented once in the 26 cDNAs resulting from secondary screening. RT-PCR data (FIG. 5) shows Mac20 mRNA is abundant in 0–2 mm anthers, is also present at very reduced levels in older anthers (2–4 mm) which are largely 'post microsphere release' and is absent in older 4–6 mm anthers. A faint signal is also present in A9-Barnase anthers (FIG. 5, lane 8) again indicating that Mac20 mRNA could be expressed prior to activity of pA9 in maize.

Sequence analysis shows that the Mac20 cDNA putatively encodes a 103 amino acid protein with a putative signal peptide predicted by the program signal P (Neilson et al., (1997) Protein engineering 10 1,6) (FIG. 6) (SEQ ID NO:18). The Mac20 DNA sequence (SEQ ID NO:17) and the putative Mac20 protein (SEQ ID NO:18) show no significant matches in DNA and protein databases. Southern analysis showed that the Mac20 cDNA hybridises to approximately 5 bands in maize BamHI and EcoRI-cut genomic DNA and with 3 bands in HindIII-cut wheat genomic DNA. Hybridisation was performed at 65° C. using a Digoxigenin-labelled probe as described in Protocols for Nucleic Acid Analysis by Nonradioactive Probes, Methods in Molecular Biology Vol 28 (1994) Ed. Isaac PG Humana Press Inc.

EXAMPLE 2

Isolation and Characterisation of the Promoter Region of the Maize Mac2 Gene.

TAIL-PCR was used to isolate sequence 5' of the Mac2 gene from maize genomic DNA. TAIL-PCR was performed according to the method of Liu et al., Plant Journal 8 457–463 (1995). Three Mac2 specific primers were designed:

Mac2tl (5'-AGT CAT CAA TGG CTA TGG CCA G-3')(SEQ ID NO:5), which binds at positions 343–322 bp of the Mac2 cDNA (FIG. 3)(SEQ ID NO:9); Mac2t2 (5'-CGT ATC TTT GCA TGA CCT CTT GG-3')(SEQ ID NO:6), which binds at 232–210 bp (FIG. 3)(SEQ ID NO:9) and Mac2t3 (5'-GTG GAG GTG CAA AAC AGC AGG T-3')(SEQ ID NO:7) which binds at 103–82 bp (FIG. 3)(SEQ ID NO:9). These primers were used individually with the degenerate primer AD1 (5'-NTCGASTWTSGWGTT-3')(SEQ ID NO:8) in three rounds of PCR starting with the combination of AD1 with the most 3' Mac2 primer and finishing with AD1 plus the most 5' Mac2 primer.

1.3 kb TAIL-PCR products were cloned into pGEM-T. 2 clones, Mac2T-1 and Mac2T-3, were completely sequenced and 6 clones Mac2T-2/4/6/7/8/9 partially sequenced. The consensus sequence obtained contains uncertainties at 5 positions: 86 bp (T or C), 347 bp (7 or 8 A residues), 555 bp (8 or 9 A residues), 665 bp (G or A) and at 754 bp (G or A) (FIG. 7)(SEQ ID NO:19). Given this sequence two primers (FIG. 7) were designed to PCR out a 1.2 kb putative promoter region from maize genomic DNA:

3' GGTCGACTTGGAATAATTTAAGTTGT 5'=new Mac2P5' (SEQ ID NO:3)

3' GATCACCATGGTACTACTCCAC 5'=Mac2P3'N (SEQ ID NO:4)

The 5' primer introduced a SalI site and the 3' primer an NcoI site (around the initiating 'ATG' codon of the putative Mac2 protein) to facilitate subsequent cloning. PCR products were cloned into pGEM-T (Promega) and sequenced. The clone containing the sequence most similar to the consensus TAIL-PCR sequence was named pMac2Prom. This sequence was identical to that of the TAIL-PCR consensus except for a T to C change at position 762 bp and the deletion of a T residue at positions 893 bp (FIG. 7)(SEQ ID NO:19).

Figure 8:
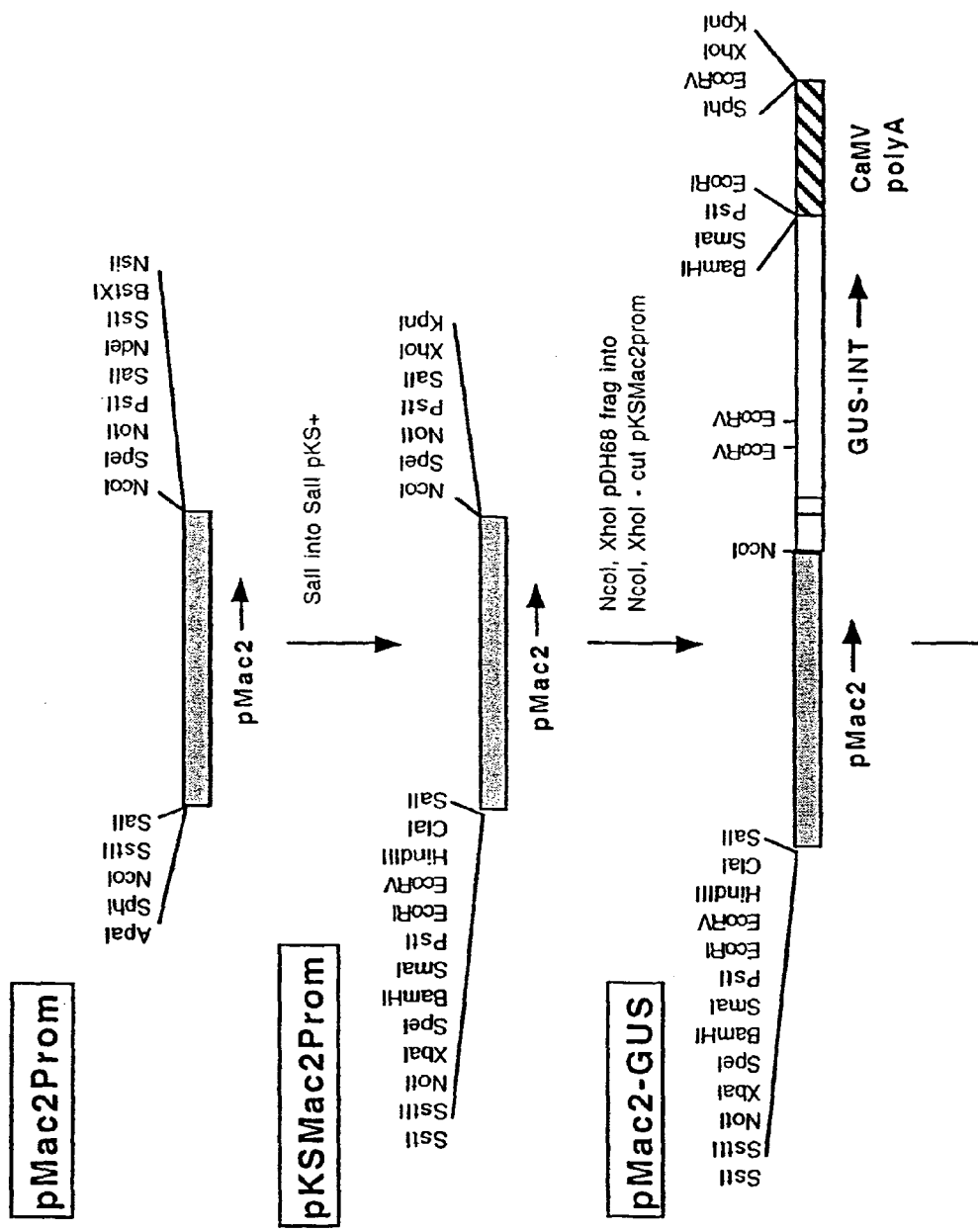
FIG. 8—is a schematic diagram of pMac2-GUSbin

To characterise the spatial and temporal expression pattern directed by the 1.2 kb Mac2 promoter region (pMac2) this region was linked to the reporter gene β-glucuronidase (Jefferson et al., EMBO J. 6 3901 (1987)) and transformed into tobacco and maize. The SalI pMac2 fragment was excised from pMac2Prom and cloned into the SalI site of pBluescript KS+ (Stratagene) forming pKSMac2Prom, such that the NcoI site of pMac2 was adjacent to the XhoI site of pBluescript KS+. An NcoI-XhoI fragment containing a GUS intron+CaMV polyadenylation sequence was cloned from pDH68 (WO99/13089) between the NcoI and XhoI sites of pKSMac2Prom forming pMac2-GUS. The pMac2-GUS-CaMVpolyA region was then excised from pMac2-GUS as a HindIII, XhoI fragment and cloned between the HindIII, SalI sites of the binary vector pBin19 (Bevan M W, (1984) Nucleic Acids Research 12, 8711–8721) forming pMac2-GUS bin (FIG. 8).

pMac2-GUSbin was transferred into the agrobacterial strain LBA4404 and transformed into *N. tabacum* using a leaf-based agrobacterial technique. Transformed *N. tabacum* plants show GUS expression in the anther tapetum. Expression commences prior to microspore release.

pMac2-GUS was also transformed into maize using a standard particle bombardment method. Transformed maize plants exhibit GUS expression in anthers of length 0–2 mm with expression localised to the tapetum. Expression of pMac2-GUS in the maize tapetum is much stronger than observed than for pA3-GUS, pA6-GUS and pA9-GUS transformed maize. This suggests that pMac2 is superior in maize to the *A. thaliana* A3 (WO 92/1179), A9 (WO 92/1179) and A6 (WO 93/02197) promoters for applications that require high-level expression in the tapetum.

EXAMPLE 3

Figure 9:
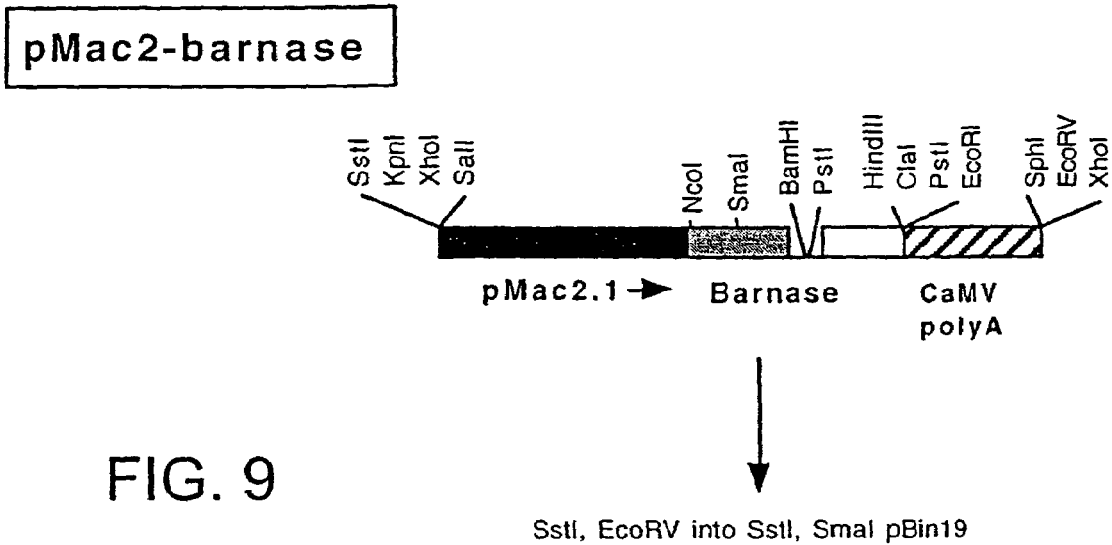
FIGS. 9A—shows a schematic diagram of pMac2-barnase bin.
FIGS. 9B–D show thin transverse sections of tobacco pMac2-barnase anthers, viewed by light microscopy.

Construction of a Chimeric pMac2-Barnase Gene and its Expression In Transgenic Plants To demonstrate the utility of the pMac2 promoter in the production of male sterile plants and to further characterise the spatial and temporal pMac2 expression pattern, pMac2 was linked to the ribonuclease barnase (Hartley, R W J. Mol. Biol. (1988) 202, 913–915). The SalI, NcoI 1224 bp Mac2 promoter fragment was excised from pMac2Prom and cloned between the SalI and NcoI sites of pWP127 (Paul et al., Plant Molecular Biology 19 611–622 (1992)). The resulting plasmid (pMac2-barnase) was digested with SstI and EcoRV and the pMac2-barnase-CaMVpolyA chimeric gene transferred into SstI, SmaI sites of the binary vector pBin19 forming pMac2-barnase bin (FIG. 9).

pMac2-barnase bin was transferred into the agrobacterial strain LBA4404 and transformed into *N. tabacum*. Transformed *N. tabacum* plants are phenotypically wild type apart from male sterility due to the ablation of the tapetum. FIG. 9 show the results of microscopic analysis of anthers from wild type and transformed tabacco plants. In the wild type (FIG. 9B) the pollen sacs are seen to have a well developed tapetum (FIG. 9B, T) and a tetrad stage microspores (FIG. 9B, M). In the transformed plant, however, the pollen sac is collapsed and lacks a clearly defined tapetum and microspores (FIG. 9C). This plant was male sterile but female fertile.

pMac2-barnase was also transformed into maize using a standard particle bombardment method. All 8 transformed plants were transformed maize plants are phenotypically wild type apart from male sterility due to the ablation of the tapetum.

EXAMPLE 4

Figure 10:
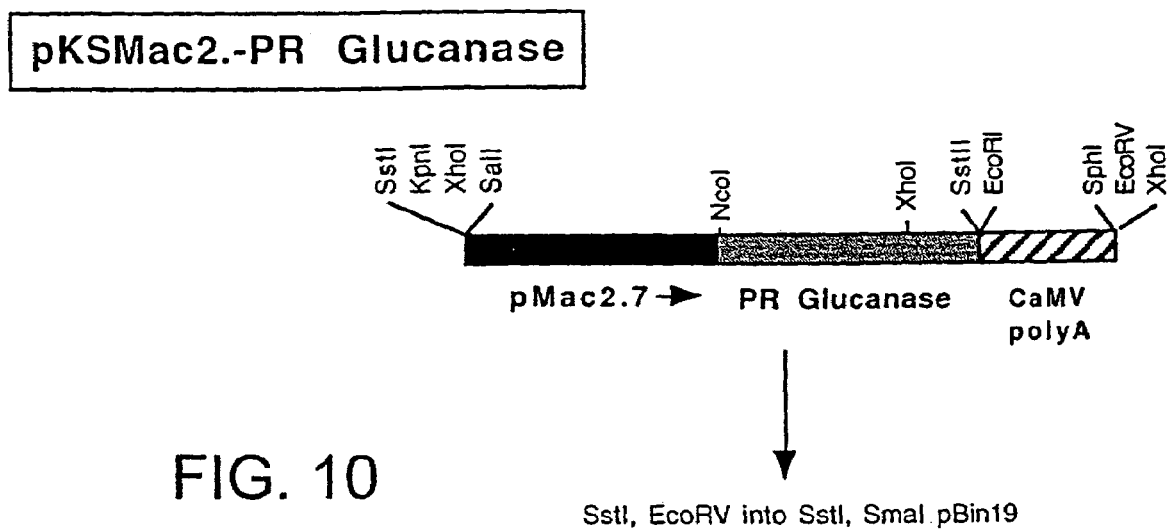
FIG. 10 A—shows a schematic diagram of the pMac2-PR-glucanase bin.
Figure 9:
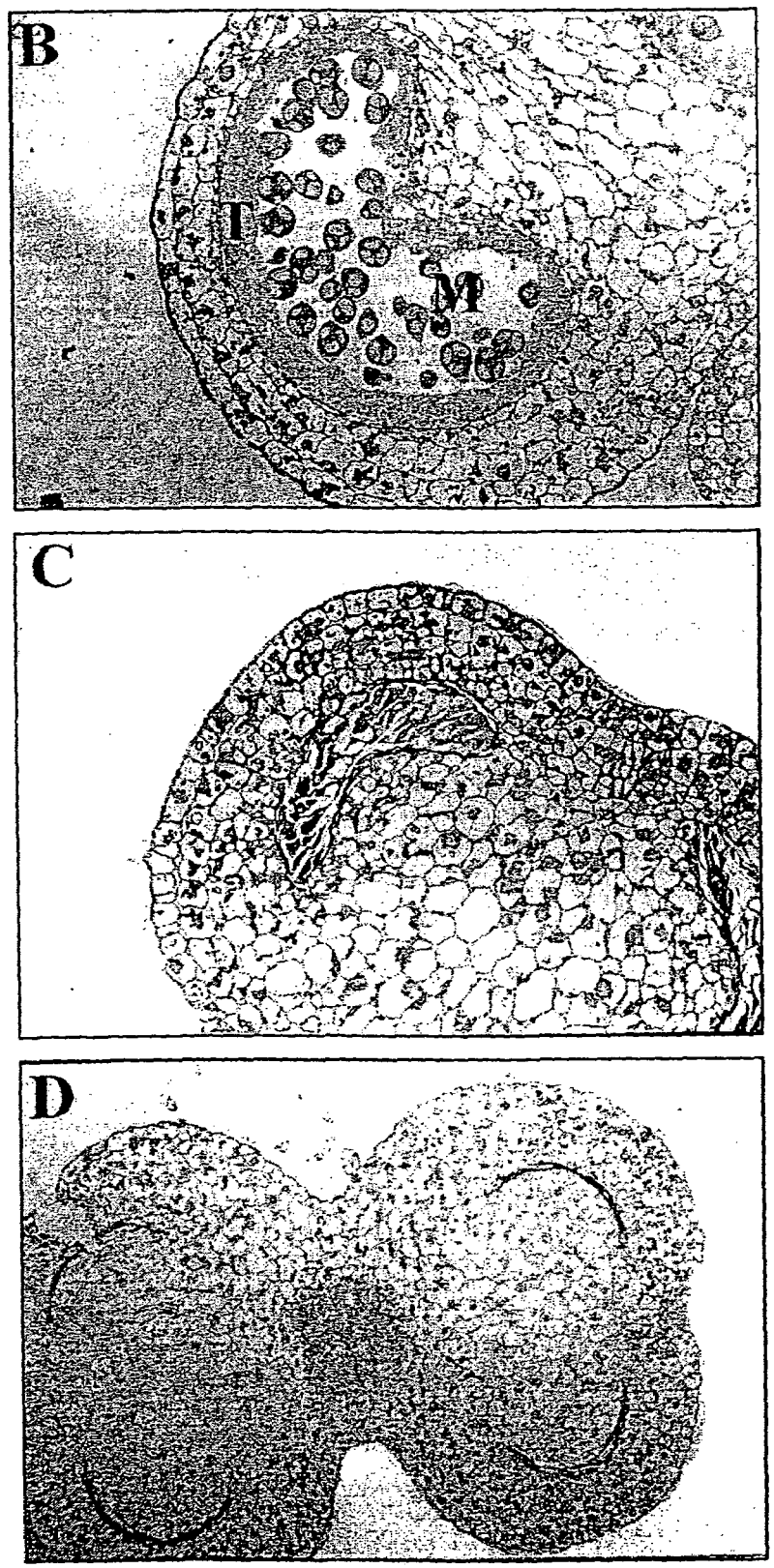
Figure 10:
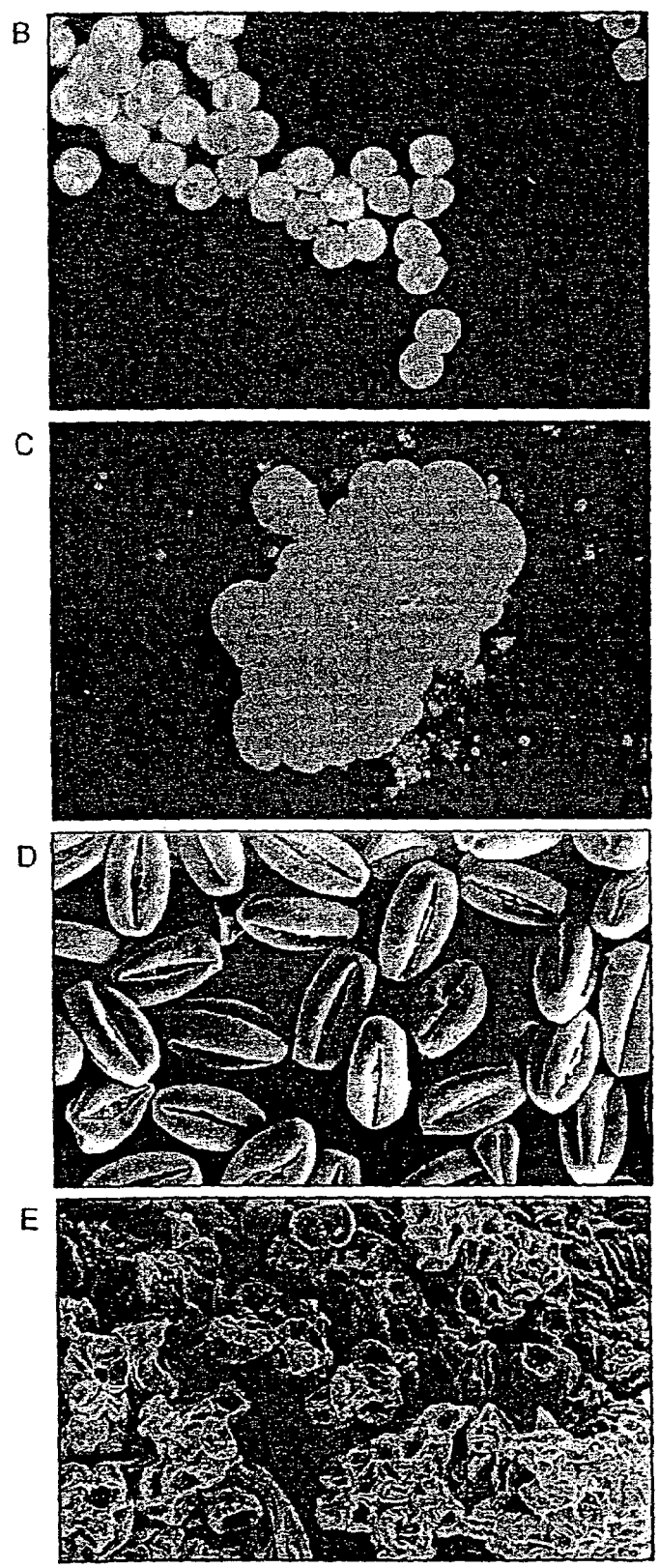

Construction of a Chimeric pMac2-PR-Glucanase Gene and its Expression in Transgenic Plants In order to create male sterile plants by the premature dissolution of callose pMac2 was linked to the PR glucanase gene (Worrall et al., (1992) Plant Cell. 4, 759–771). The SalI, NcoI 1224 bp Mac2 promoter fragment was excised from pMac2Prom and cloned between the SalI and NcoI sites of pDW80PR (Worrall et al., (1992) Plant Cell. 4, 759–771). The resulting plasmid (pMac2-PRG) was digested with SstI and EcoRV and the pMac2-PR Glucanase-CaMVpolyA chimeric gene transferred into SstI, SmaI-cut pBin 19 forming pMac2-PRG bin (FIG. 10).

pMac2-PRG bin was transferred into the agrobacterial strain LBA4404 and transformed into *N. tabacum*. Transformed *N. tabacum* plants are phenotypically wild type apart from male sterility. The results of microscopic examination of anthers from transformed plants is shown in FIG. 10. In the wild type, (FIG. 10B), the tetrads of the anthers are separate and have a regular morphology. Each tetrad has highly fluorescent callosic cross walls and callosic outer walls. In contrast, the tetrads extruded from anthers of transformed plants are clumped together, as judged by the aniline blue induced fluorescence. The tetrads lack both callosic cross walls and outer walls (FIG. 10C).

The scanning electron micrographs of tobacco microspores/pollen from both wild type and pMAC2-PR glucanase plants are shown in FIGS. 10D and E, respectively. The wild type is seen to have well developed pollen grains with uniform morphology, each grain being separate and plump with a smooth pollen wall with frequent small holes.

In contrast, the microspores of the transformed plant are very irregular, and appear to be fused together in small clumps. They also appear collapsed with very irregular pollen walls.

The severely reduced levels of callose surrounding cells undergoing meiosis and surrounding tetrads leads to subsequent death of microspores and male sterility. The frequency of complete male sterility was much higher than that observed using pA9-PR glucanase (Worrall et al, supra). Cytologically the phenotype of fused tetrads resembles that produced by pA9-PR glucanase in tomato. In this species pA9-PR glucanase produces a high frequency of complete sterility.

pMac2-PRG was transformed into maize using a standard particle bombardment method. Transformed maize plants are phenotypically wild type apart from male sterility due to reduced callose levels in the anther prior to microspore release.

EXAMPLE 5

Expression of a Modified Mac2 Protein in Transgenic Plants.

The Mac2 putative protein shows homology to the type 1-RIPs (Example 1). The possession of a signal peptide in the Mac2 protein targets the Mac2 protein for secretion into the endoplasmic reticulum thus preventing access of Mac2 to the tapetal cell ribosomes. Removal of this signal peptide will allow the Mac2 protein to accumulate in the cytosol and inactivate the ribosomes causing cell death. Thus a Mac2 protein lacking a signal peptide (ΔMac2)(SEQ ID NO:26) is generally useful as a cellular ablator and provides a plant derived alternative to the bacterial barnase protein. To demonstrate the utility of this modified Mac2 protein it is used to generate male sterile plants by tapetal cell ablation. Tapetal-specific promoters that could be used include pMac2 itself or promoters isolated from *Arabidopsis* such as pA9 (Paul et al., Plant Molecular Biology 19 611–622 (1992)). A pA9-ΔMac2 fusion is constructed as follows. The following primers were used to PCR a Mac2 region encoding a Mac2 protein lacking the signal peptide (FIG. 11*a*)(SEQ ID NO:25; SEQ ID NO:26):

5' CCCATGGCCTCCACCGCCTATCC 3' ΔMac2F (SEQ ID NO:1) and

5' GCCGCGGTAATTACCAGTATCTACTTCC 3' ΔMac2R (SEQ ID NO:2)

Figure 11B:
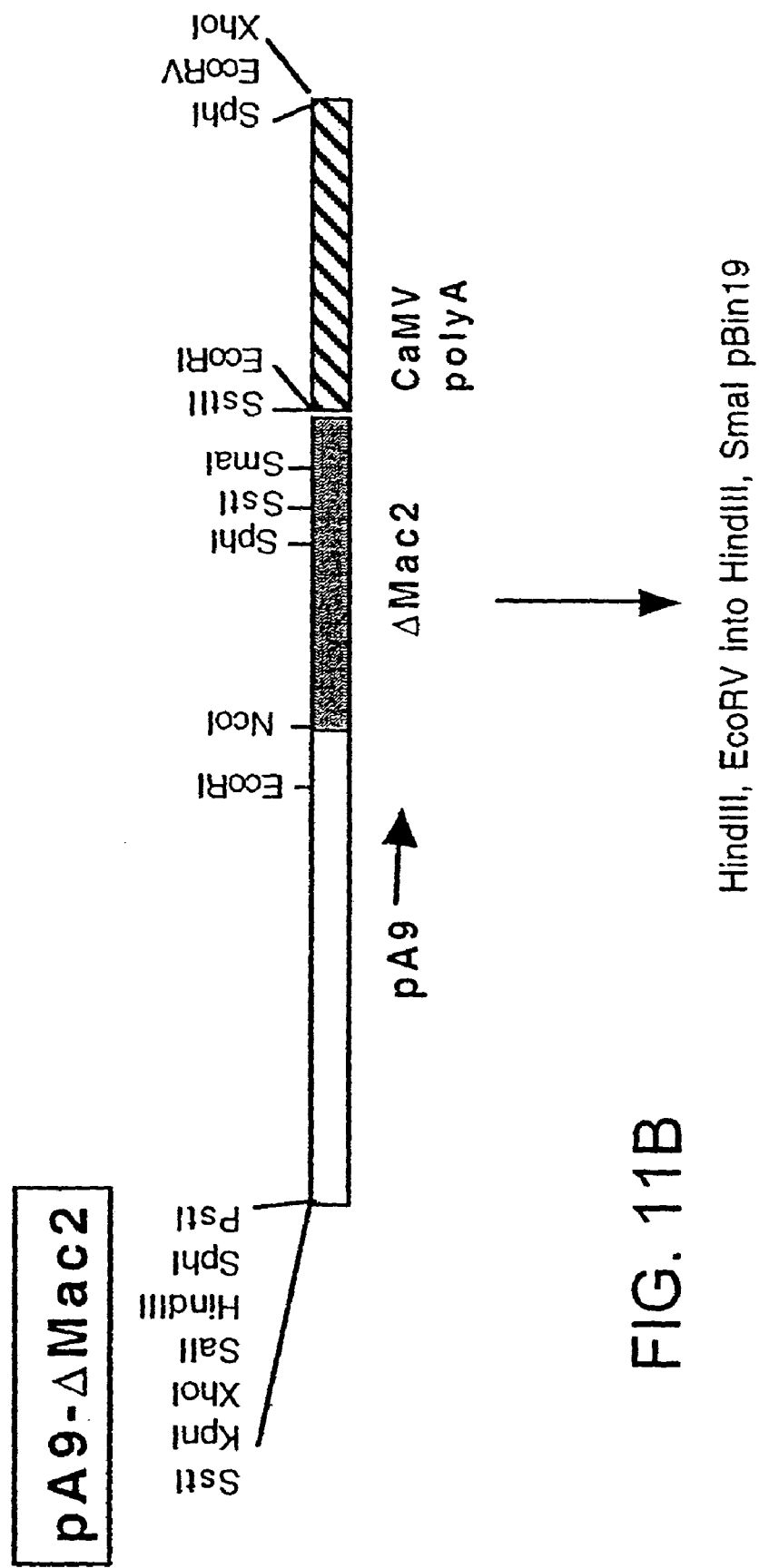
FIG. 11—shows A) Partial DNA sequence of pMac2 (SEQ ID NO:23; SEQ ID NO:25) showing where the ΔMac2F (SEQ ID NO:1) and ΔMac2R primers bind (SEQ ID NO:27); and B) a schematic diagram of pA9-ΔMac2.

The 843 bp PCR product was digested with NcoI and SstII and cloned between the NcoI and SstII sites of pWP112 (WO 92/11379) forming pA9-ΔMac2 (FIG. 11*b*). The pA9-ΔMac2-CaMV polyA region of pA9-ΔMac2 was excised as a HindIII, EcoRV fragment and cloned between the HindIII and SmaI sites of pBin19 forming pA9-ΔMac2bin.

pA9-ΔMac2bin was transferred into the agrobacterial strain LBA4404 and transformed into *N. tabacum*. Transformed *N. tabacum* plants are phenotypically wild type apart from male sterility due to the ablation of the tapetum.

pA9-ΔMac2 was also transformed into maize using a standard particle bombardment method. Transformed maize plants are phenotypically wild type apart from male sterility due to the ablation of the tapetum.

EXAMPLE 6

Isolation and Characterisation of the Promoter Region of a Maize Mac20 Gene.

Inverse PCR (IPCR) was used to isolate the promoter region of a Mac20 gene. Maize genomic DNA was digested with BalI, which cleaves inside of Mac20 and recircularised with T4 DNA ligase. Divergent primer pairs which bind within Mac20 were used to PCR out a Mac20 fragment. Sequence analysis (FIG. 12)(SEQ ID NO:28) showed that this fragment was 96% identical to Mac20 within the region of overlap. RT-PCR analysis, with primers specific to the coding regions of the IPCR Mac20 gene, showed that the IPCR Mac20 gene has the same temporal and spatial expression pattern as the Mac2 gene. A longer promoter region is then obtained from maize genomic DNA by TAIL PCR essentially as described in Example 2.

What is claimed is:

1. A recombinant or isolated nucleic acid molecule comprising a pMAC2 promoter sequence comprising nucleotides 35 to 1258 of SEQ ID NO:19.

2. A nucleic acid molecule as claimed in claim 1 which is a DNA molecule.

3. A nucleic acid molecule as claimed in claim 1 which further comprises a nucleic acid, which when expressed results in male sterility in a plant.

4. A nucleic acid molecule as claimed in claim 3 wherein the male sterility nucleic acid codes for a lytic enzyme.

5. A nucleic acid molecule as claimed in claim 4 wherein the lytic enzyme is glucanase or barnase.

6. A nucleic acid as claimed in claim 5 wherein the glucanase is PR-glucanase.

7. A vector comprising a nucleic acid molecule as defined in claim 1.

8. A host cell transformed with a vector as defined in claim 7.

9. A host cell as claimed in claim 8 which is a plant cell.

10. A host cell as claimed in claim 9 which is a monocot plant cell.

11. A plant comprising one or more plant cells as defined in claim 9.

12. A method of transforming a host cell comprising introducing the nucleic acid molecule as defined in claim 1 into the host cell with a particle gun.

13. A method of producing a male sterile plant comprising:
   (i) introducing the nucleic acid molecule as defined in claim 3 into a plant cell with a particle gun; and
   (ii) generating said male sterile plant from the transformed plant cell.

14. The method according to claim 13, wherein the male sterile plant is a monocot.

* * * * *

SEQUENCE LISTING

<160> NUMBER OF SEQ ID NOS: 29

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
cccatggcct ccaccgccta tcc                    23

<210> SEQ ID NO 2
<211> LENGTH: 28
<212> TYPE: DNA
<213> ORGANISM: Artificial Sequence
<220> FEATURE:
<223> OTHER INFORMATION: Primer

<400> SEQUENCE: 2
gccgcggtaa ttaccagtat ctacttcc               28

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
ggtcgacttg gaataattta agttgt                 26

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
gatcaccatg gtactactcc ac                     22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
agtcatcaat ggctatggcc ag                     22

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
cgtatctttg catgacctct tgg                    23

<210> SEQ ID NO 7
<211> LENGTH: 22

```
<212> TYPE: DNA
<213> ORGANISM: Artificial Sequence
<220> FEATURE:
<223> OTHER INFORMATION: Primer

<400> SEQUENCE: 7
gtggaggtgc aaaacagcag gt                                             22

<210> SEQ ID NO 8
<211> LENGTH: 15
<212> TYPE: DNA
<213> ORGANISM: Artificial Sequence
<220> FEATURE:
<223> OTHER INFORMATION: Primer
<221> NAME/KEY: misc_feature
<222> LOCATION: (1)..(1)
<223> OTHER INFORMATION: May be any nucleotide

<400> SEQUENCE: 8
ntcgastwts gwgtt                                                     15

<210> SEQ ID NO 9
<211> LENGTH: 1050
<212> TYPE: DNA
<213> ORGANISM: Zea mays
<220> FEATURE:
<221> NAME/KEY: CDS
<222> LOCATION: (31)..(924)

<400> SEQUENCE: 9
```

| | | | | | | | | | | | | | | | | |
|---|---|---|---|---|---|---|---|---|---|---|---|---|---|---|---|---|
| gaggcatcgc | caagcaagtg | gagtagtacg | atg | gtg | atc | aat | agg | ccg | cag | tta | | | | | | 54 |
| | | | Met | Val | Ile | Asn | Arg | Pro | Gln | Leu | | | | | | |
| | | | 1 | | | | 5 | | | | | | | | | |
| gtt | tct | agt | ata | ata | gtc | tgt | ttt | gca | acc | tgc | tgt | ttt | gca | cct | cca | 102 |
| Val | Ser | Ser | Ile | Ile | Val | Cys | Phe | Ala | Thr | Cys | Cys | Phe | Ala | Pro | Pro | |
| | 10 | | | | | 15 | | | | | 20 | | | | | |
| ccg | cct | atc | cac | cac | atg | tat | gtt | gac | atc | act | act | cag | act | tac | aat | 150 |
| Pro | Pro | Ile | His | His | Met | Tyr | Val | Asp | Ile | Thr | Thr | Gln | Thr | Tyr | Asn | |
| 25 | | | | | 30 | | | | | 35 | | | | | 40 | |
| agt | tta | tat | att | gag | ttt | gca | aat | ctg | ctc | aag | atc | ccg | ata | ggg | cct | 198 |
| Ser | Leu | Tyr | Ile | Glu | Phe | Ala | Asn | Leu | Leu | Lys | Ile | Pro | Ile | Gly | Pro | |
| | | | | 45 | | | | | 50 | | | | | 55 | | |
| gta | tat | gat | ccc | caa | gag | gtc | atg | caa | aga | tac | gtt | ctc | gga | cct | cgc | 246 |
| Val | Tyr | Asp | Pro | Gln | Glu | Val | Met | Gln | Arg | Tyr | Val | Leu | Gly | Pro | Arg | |
| | | | 60 | | | | | 65 | | | | | 70 | | | |
| cgc | ttt | ggt | ttt | tat | gat | gag | cca | cct | gaa | tgg | ata | tat | att | cat | gtc | 294 |
| Arg | Phe | Gly | Phe | Tyr | Asp | Glu | Pro | Pro | Glu | Trp | Ile | Tyr | Ile | His | Val | |
| | | 75 | | | | | 80 | | | | | 85 | | | | |
| gtc | ggg | gaa | gaa | caa | gac | aag | gta | act | ctg | gcc | ata | gcc | att | gat | gac | 342 |
| Val | Gly | Glu | Glu | Gln | Asp | Lys | Val | Thr | Leu | Ala | Ile | Ala | Ile | Asp | Asp | |
| | 90 | | | | | 95 | | | | | 100 | | | | | |
| tta | tgt | ctt | att | ggc | ttc | agt | aat | gct | agt | gac | cat | tgg | tac | aag | ttt | 390 |
| Leu | Cys | Leu | Ile | Gly | Phe | Ser | Asn | Ala | Ser | Asp | His | Trp | Tyr | Lys | Phe | |
| 105 | | | | | 110 | | | | | 115 | | | | | 120 | |
| aat | gga | cag | tca | tca | tcg | ttc | aaa | ggt | ttg | ccg | gga | gcc | acc | gtg | cta | 438 |
| Asn | Gly | Gln | Ser | Ser | Ser | Phe | Lys | Gly | Leu | Pro | Gly | Ala | Thr | Val | Leu | |
| | | | | 125 | | | | | 130 | | | | | 135 | | |
| ccg | atc | aga | caa | aat | tat | caa | gat | ttg | atc | aaa | gga | cac | gcc | aac | ctt | 486 |
| Pro | Ile | Arg | Gln | Asn | Tyr | Gln | Asp | Leu | Ile | Lys | Gly | His | Ala | Asn | Leu | |
| | | | 140 | | | | | 145 | | | | | 150 | | | |
| tgg | aag | gtt | cct | ctg | ggg | aag | aag | tca | gcc | ata | cat | gcc | acc | aag | cag | 534 |
| Trp | Lys | Val | Pro | Leu | Gly | Lys | Lys | Ser | Ala | Ile | His | Ala | Thr | Lys | Gln | |
| | | 155 | | | | | 160 | | | | | 165 | | | | |

```
ctt gcg acg tat gac cga gcc gtc acc cct gac tcc gaa ctc aag gac      582
Leu Ala Thr Tyr Asp Arg Ala Val Thr Pro Asp Ser Glu Leu Lys Asp
    170                 175                 180 ggg ctg gtt agg ttc gtg gtg atg atg tgt gaa ggc atg cgg ttc cga      630
Gly Leu Val Arg Phe Val Val Met Met Cys Glu Gly Met Arg Phe Arg
185                 190                 195                 200 tcg atc cgc gac atg ttc tca tcg ttg tcg ggc aat aac tgg gag gag      678
Ser Ile Arg Asp Met Phe Ser Ser Leu Ser Gly Asn Asn Trp Glu Glu
                205                 210                 215 gag acc ttc atc act gag ctc caa gca aaa tct gtc gtc tac tgg tca      726
Glu Thr Phe Ile Thr Glu Leu Gln Ala Lys Ser Val Val Tyr Trp Ser
            220                 225                 230 caa ctc tcg atg cta ctc att cgg tgg gag cta acc gga agg ctg ccc      774
Gln Leu Ser Met Leu Leu Ile Arg Trp Glu Leu Thr Gly Arg Leu Pro
        235                 240                 245 ggg ggg cca aaa tgg ggt gct gtt gat ggt cga tat aac agt atg gct      822
Gly Gly Pro Lys Trp Gly Ala Val Asp Gly Arg Tyr Asn Ser Met Ala
    250                 255                 260 aag cat gtc caa gag gct att aat gtc aat gat gcg aac gat gct ttg      870
Lys His Val Gln Glu Ala Ile Asn Val Asn Asp Ala Asn Asp Ala Leu
265                 270                 275                 280 aca atc att gat ttt ctg ctt cgc cca aca gag gaa gta gat act ggt      918
Thr Ile Ile Asp Phe Leu Leu Arg Pro Thr Glu Glu Val Asp Thr Gly
                285                 290                 295 aat tag ttttaatata tataattatt agttacgtca tcgatctgtt gtaatagttt      974
Asn atatatacct ctaatattaa aaaagtaaaa tttcagcctt gtttccaaaa aaaaaaaaaa     1034
aaaaaaaaaa aaaaa                                                      1050

<210> SEQ ID NO 10
<211> LENGTH: 297
<212> TYPE: PRT
<213> ORGANISM: Zea mays

<400> SEQUENCE: 10

Met Val Ile Asn Arg Pro Gln Leu Val Ser Ile Ile Val Cys Phe
1               5                   10                  15

Ala Thr Cys Cys Phe Ala Pro Pro Pro Ile His His Met Tyr Val
                20                  25                  30

Asp Ile Thr Thr Gln Thr Tyr Asn Ser Leu Tyr Ile Glu Phe Ala Asn
            35                  40                  45

Leu Leu Lys Ile Pro Ile Gly Pro Val Tyr Asp Pro Gln Glu Val Met
 50                  55                  60

Gln Arg Tyr Val Leu Gly Pro Arg Arg Phe Gly Phe Tyr Asp Glu Pro
 65                  70                  75                  80

Pro Glu Trp Ile Tyr Ile His Val Val Gly Glu Gln Asp Lys Val
                85                  90                  95

Thr Leu Ala Ile Ala Ile Asp Asp Leu Cys Leu Ile Gly Phe Ser Asn
            100                 105                 110

Ala Ser Asp His Trp Tyr Lys Phe Asn Gly Gln Ser Ser Ser Phe Lys
            115                 120                 125

Gly Leu Pro Gly Ala Thr Val Leu Pro Ile Arg Gln Asn Tyr Gln Asp
    130                 135                 140

Leu Ile Lys Gly His Ala Asn Leu Trp Lys Val Pro Leu Gly Lys Lys
145                 150                 155                 160

Ser Ala Ile His Ala Thr Lys Gln Leu Ala Thr Tyr Asp Arg Ala Val
                165                 170                 175
```

-continued

```
Thr Pro Asp Ser Glu Leu Lys Asp Gly Leu Val Arg Phe Val Val Met
            180                 185                 190
Met Cys Glu Gly Met Arg Phe Arg Ser Ile Arg Asp Met Phe Ser Ser
        195                 200                 205
Leu Ser Gly Asn Asn Trp Glu Glu Thr Phe Ile Thr Glu Leu Gln
    210                 215                 220
Ala Lys Ser Val Val Tyr Trp Ser Gln Leu Ser Met Leu Leu Ile Arg
225                 230                 235                 240
Trp Glu Leu Thr Gly Arg Leu Pro Gly Pro Lys Trp Gly Ala Val
            245                 250                 255
Asp Gly Arg Tyr Asn Ser Met Ala Lys His Val Gln Glu Ala Ile Asn
            260                 265                 270
Val Asn Asp Ala Asn Asp Ala Leu Thr Ile Ile Asp Phe Leu Leu Arg
            275                 280                 285
Pro Thr Glu Glu Val Asp Thr Gly Asn
            290                 295
```

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
acctgctgtt ttgcacctcc ac                                              22

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ccaagaggtc atgcaaagat acg                                             23

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
ctggccatag ccattgatga ct                                              22

<210> SEQ ID NO 14
<211> LENGTH: 300
<212> TYPE: PRT
<213> ORGANISM: Zea mays

<400> SEQUENCE: 14

```
Met Ala Glu Ile Thr Leu Glu Pro Ser Asp Leu Met Ala Gln Thr Asn
  1               5                  10                  15
Lys Arg Ile Val Pro Lys Phe Thr Glu Ile Phe Pro Val Glu Asp Ala
            20                  25                  30
Asn Tyr Pro Tyr Ser Ala Phe Ile Ala Ser Val Arg Lys Asp Val Ile
        35                  40                  45
Lys His Cys Thr Asp His Lys Gly Ile Phe Gln Pro Val Leu Pro Pro
```

-continued

```
              50                  55                  60
Glu Lys Lys Val Pro Glu Leu Trp Leu Tyr Thr Glu Leu Lys Thr Arg
 65                  70                  75                  80

Thr Ser Ser Ile Thr Leu Ala Ile Arg Met Asp Asn Leu Tyr Leu Val
                 85                  90                  95

Gly Phe Arg Thr Pro Gly Gly Val Trp Trp Glu Phe Gly Lys Asp Gly
            100                 105                 110

Asp Thr His Leu Leu Gly Asp Asn Pro Arg Trp Leu Gly Phe Gly Gly
            115                 120                 125

Arg Tyr Gln Asp Leu Ile Gly Asn Lys Gly Leu Glu Thr Val Thr Met
130                 135                 140

Gly Arg Ala Glu Met Thr Arg Ala Val Asn Asp Leu Ala Lys Lys Lys
145                 150                 155                 160

Lys Met Ala Thr Leu Glu Glu Glu Val Gln Met Gln Met Gln Met
                165                 170                 175

Pro Glu Ala Ala Asp Leu Ala Ala Ala Ala Ala Asp Pro Gln Ala
            180                 185                 190

Asp Thr Lys Ser Lys Leu Val Lys Leu Val Val Met Val Cys Glu Gly
            195                 200                 205

Leu Arg Phe Asn Thr Val Ser Arg Thr Val Asp Ala Gly Phe Asn Ser
210                 215                 220

Gln His Gly Val Thr Leu Thr Val Thr Gln Gly Lys Gln Val Gln Lys
225                 230                 235                 240

Trp Asp Arg Ile Ser Lys Ala Ala Phe Glu Trp Ala Asp His Pro Thr
                245                 250                 255

Ala Val Ile Pro Asp Met Gln Lys Leu Gly Ile Lys Asp Lys Asn Glu
            260                 265                 270

Ala Ala Arg Ile Val Ala Leu Val Lys Asn Gln Thr Thr Ala Cys Ala
            275                 280                 285

Thr Ala Ala Ser Ala Asp Asn Asp Asp Glu Ala
290                 295                 300
```

<210> SEQ ID NO 15
<211> LENGTH: 281
<212> TYPE: PRT
<213> ORGANISM: Hordeum vulgare

<400> SEQUENCE: 15

```
Met Ala Ala Lys Met Ala Lys Asn Val Asp Lys Pro Leu Phe Thr Ala
  1               5                  10                  15

Thr Phe Asn Val Gln Ala Ser Ser Ala Asp Tyr Ala Thr Phe Ile Ala
                 20                  25                  30

Gly Ile Arg Asn Lys Leu Arg Asn Pro Ala His Phe Ser His Asn Arg
            35                  40                  45

Pro Val Leu Pro Pro Val Glu Pro Asn Val Pro Pro Ser Arg Trp Phe
 50                  55                  60

His Val Val Leu Lys Ala Ser Pro Thr Ser Ala Gly Leu Thr Leu Ala
 65                  70                  75                  80

Ile Arg Ala Asp Asn Ile Tyr Leu Glu Gly Phe Lys Ser Ser Asp Gly
                 85                  90                  95

Thr Trp Trp Glu Leu Thr Pro Gly Leu Ile Pro Gly Ala Thr Tyr Val
            100                 105                 110

Gly Phe Gly Gly Thr Tyr Arg Asp Leu Leu Gly Asp Thr Asp Lys Leu
            115                 120                 125
```

```
Thr Asn Val Ala Leu Gly Arg Gln Gln Leu Ala Asp Ala Val Thr Ala
    130                 135                 140

Leu His Gly Arg Thr Lys Ala Asp Lys Pro Ser Gly Pro Lys Gln Gln
145                 150                 155                 160

Gln Ala Arg Glu Ala Val Thr Thr Leu Leu Met Val Asn Glu Ala
                165                 170                 175

Thr Arg Phe Gln Thr Val Ser Gly Phe Val Ala Gly Leu Leu His Pro
            180                 185                 190

Lys Ala Val Glu Lys Lys Ser Gly Lys Ile Gly Asn Glu Met Lys Ala
        195                 200                 205

Gln Val Asn Gly Trp Gln Asp Leu Ser Ala Ala Leu Leu Lys Thr Asp
    210                 215                 220

Val Lys Pro Pro Gly Lys Ser Pro Ala Lys Phe Ala Pro Ile Glu
225                 230                 235                 240

Lys Met Gly Val Arg Thr Ala Val Gln Ala Ala Asn Thr Leu Gly Ile
                245                 250                 255

Leu Leu Phe Val Glu Val Pro Gly Gly Leu Thr Val Ala Lys Ala Leu
            260                 265                 270

Glu Leu Phe His Ala Ser Gly Gly Lys
        275                 280

<210> SEQ ID NO 16
<211> LENGTH: 275
<212> TYPE: PRT
<213> ORGANISM: Triticum aestivum

<400> SEQUENCE: 16

Met Ala Lys Asn Val Asp Lys Pro Leu Phe Thr Ala Thr Phe Asn Val
1               5                   10                  15

Gln Ala Ser Ser Ala Asp Tyr Val Thr Phe Ile Asn Gly Ile Arg Asn
            20                  25                  30

Lys Leu Arg Asn Pro Gly His Ser His Asn Arg Pro Val Leu Pro
        35                  40                  45

Pro Ile Glu Pro Asn Val Pro Pro Ser Arg Trp Phe His Ile Val Leu
    50                  55                  60

Lys Thr Ser Pro Ala Ser Thr Gly Leu Thr Leu Ala Thr Arg Ala Asp
65                  70                  75                  80

Asn Leu Tyr Trp Glu Gly Phe Lys Ser Ser Asp Gly Thr Trp Trp Glu
                85                  90                  95

Leu Thr Pro Gly Leu Ile Pro Gly Ala Thr His Val Gly Phe Gly Gly
            100                 105                 110

Thr Tyr Arg Asp Leu Leu Gly Asp Thr Asp Lys Leu Thr Asn Val Ala
        115                 120                 125

Leu Gly Arg Gln Gln Met Ala Asp Ala Val Thr Ala Leu Tyr Gly Arg
    130                 135                 140

Thr Lys Ala Asp Lys Thr Ser Gly Pro Lys Gln Gln Ala Arg Glu
145                 150                 155                 160

Ala Val Thr Thr Leu Leu Met Val His Glu Ala Thr Arg Phe Gln
                165                 170                 175

Thr Val Ser Gly Phe Val Ala Gly Val Leu His Pro Lys Glu Lys Lys
            180                 185                 190

Ser Gly Lys Ile Gly Asn Glu Met Lys Ala Gln Val Asn Gly Trp Gln
        195                 200                 205

Asp Leu Ser Glu Ala Leu Leu Lys Thr Asp Ala Asn Ala Pro Pro Gly
    210                 215                 220
```

```
Lys Ala Pro Ala Lys Phe Thr Pro Ile Glu Lys Met Gly Val Arg Thr
225                 230                 235                 240

Ala Glu Gln Ala Ala Ala Thr Leu Gly Ile Leu Leu Phe Val Gln Val
                245                 250                 255

Pro Gly Gly Met Thr Val Ala Gln Ala Leu Glu Leu Phe His Lys Ser
            260                 265                 270

Gly Gly Lys
        275

<210> SEQ ID NO 17
<211> LENGTH: 839
<212> TYPE: DNA
<213> ORGANISM: Zea mays
<220> FEATURE:
<221> NAME/KEY: CDS
<222> LOCATION: (131)..(442)

<400> SEQUENCE: 17
```

| | |
|---|---:|
| gcttccaaac tagaacaaca caatccaaga gcgcgtggga gagcgagcga aaaagcaaga | 60 |
| tcaagagaga gcgatcgaga aagacaaca caagaagcaa taaagagtcg gggaccggag | 120 |
| cgaaggaccg atg gcc gtc tac ttc agc atc acc gcc ttc ctt gtc gtc | 169 |
|               Met Ala Val Tyr Phe Ser Ile Thr Ala Phe Leu Val Val | |
|                1           5              10 | |
| atc atc ctg gtc ctg gcc gcg tgc ggc gtc gtt ttt gtc aat gtc gtc | 217 |
| Ile Ile Leu Val Leu Ala Ala Cys Gly Val Val Phe Val Asn Val Val | |
|  15               20              25 | |
| gtc atc atc tgg ggc ttc gcc ctc gcc gcg tct ccg ttc tcg ttc tta | 265 |
| Val Ile Ile Trp Gly Phe Ala Leu Ala Ala Ser Pro Phe Ser Phe Leu | |
|      30              35             40              45 | |
| ctg tcc aag gtc aag tgg cat tcg cgg cta ccg cca tcg tca cgg atg | 313 |
| Leu Ser Lys Val Lys Trp His Ser Arg Leu Pro Pro Ser Ser Arg Met | |
|           50              55              60 | |
| ccg gag gag gag ttg atg ttt ccg tcg cac tgg ttc gac gaa aca cta | 361 |
| Pro Glu Glu Glu Leu Met Phe Pro Ser His Trp Phe Asp Glu Thr Leu | |
|                65              70              75 | |
| ctg cag gcg gac tcg gag gag gag gtg ctg ctt ccg acg cac tgg ttc | 409 |
| Leu Gln Ala Asp Ser Glu Glu Glu Val Leu Leu Pro Thr His Trp Phe | |
|         80              85              90 | |
| gac gaa aca cta ttg cag gag tct aca tcg tag tagacagccg tgatcgagct | 462 |
| Asp Glu Thr Leu Leu Gln Glu Ser Thr Ser | |
|         95              100 | |
| tggatgggac ggagttgacg cgtcctttgg aactggatca gttcttgttc ttgaagttga | 522 |
| aggattcttt cgacgtttct gtcactgcat ttttggaact gatcaagggt agtatgctgg | 582 |
| tgcgtgtcgc ctgatagtct agattagtta ttgaaacatt ttttcattgt ttctgccatt | 642 |
| cgctttcttg gaaactatcg agcttagctg cgttcatgct cttttgttca gattcgtgtt | 702 |
| cagctgcgac gaactgaatt tcttgatgcc aagaaacgat ggtttgttag tccttggatc | 762 |
| agttagagtg ttctgactga agcaaaaaga tccttggttc attgctcttc caaaaaaaa | 822 |
| aaaaaaaaaa aaaaaaa | 839 |

```
<210> SEQ ID NO 18
<211> LENGTH: 103
<212> TYPE: PRT
<213> ORGANISM: Zea mays

<400> SEQUENCE: 18

Met Ala Val Tyr Phe Ser Ile Thr Ala Phe Leu Val Val Ile Ile Leu
```

```
                1               5              10              15
             Val Leu Ala Ala Cys Gly Val Val Phe Val Asn Val Val Ile Ile
                          20                  25                  30

Trp Gly Phe Ala Leu Ala Ala Ser Pro Phe Ser Phe Leu Leu Ser Lys
                      35                  40                  45

Val Lys Trp His Ser Arg Leu Pro Pro Ser Ser Arg Met Pro Glu Glu
                  50                  55                  60

Glu Leu Met Phe Pro Ser His Trp Phe Asp Glu Thr Leu Leu Gln Ala
              65                  70                  75                  80

Asp Ser Glu Glu Glu Val Leu Leu Pro Thr His Trp Phe Asp Glu Thr
                          85                  90                  95

Leu Leu Gln Glu Ser Thr Ser
                         100
```

<210> SEQ ID NO 19
<211> LENGTH: 1321
<212> TYPE: DNA
<213> ORGANISM: Zea mays
<220> FEATURE:
<221> NAME/KEY: CDS
<222> LOCATION: (1250)..(1321)
<221> NAME/KEY: unsure
<222> LOCATION: (347)..(354)
<223> OTHER INFORMATION: 7 or 8 a residues
<221> NAME/KEY: unsure
<222> LOCATION: (555)..(563)
<223> OTHER INFORMATION: 8 or 9 a residues
<221> NAME/KEY: misc_difference
<222> LOCATION: (762)
<223> OTHER INFORMATION: c in pMac2Prom
<221> NAME/KEY: misc_difference
<222> LOCATION: (893)
<223> OTHER INFORMATION: t residue is deleted in pMac2Prom

<400> SEQUENCE: 19

```
gtcgagtatg gagttcgaac ccgtgtatac aagtgatgca cttggaataa tttaagttgt      60
ggaaatgatg aatttattat cgaggyagca taatttaaaa attggaactg ttgaaggcta     120
agtatatttt tgttcccaat atatatttat gaacttgcta aattaaagtt tatggagctt     180
ttttttttgaa gtaatggaga tgctctaaag ggaggtcatt ttgcaaacaa atttaagaat    240
aaaaaaggaa aacacaggag cagctatagg taaggtgcta taatcgaaaa agaattgttg     300
tactaggtag cattcgagga gcattttgta gctagatgat taaggtaaaa aaaagtgtga     360
ctgctgcggc caaagaagca tgcgcaaatc tttctctcgg ctcccttgc atgcacaacc      420
tactcagtct ttagaaaaat aaagttttca aactagtcct tagggtggaa ttgattctag     480
cgtttggtta cggaggccat ctccattagt tcccgaaaaa gaagttccta aaattaattt     540
agggtgttaa taacaaaaaa aaataatgct ccaacaattt cttgaataag attatcaaat     600
atactaaata tatatctcta ttaatgtatt ctctaaactt ggggagttgt ttcgtatgcc     660
caatraccta ttctgctcat aaatcgtacc gtgaaataat tacttgtcag ccatatgagt     720
tcgcaccgtg tatacaagtg atgcacttag aatratttaa gttgcggaaa tgatgaattt     780
attatcgagg tagcataatt taaaaactgg aactgttgga ggttaagtat attttttgttc    840
ctaatatata tttatgaact tgctaaatta agtttgtgg agcttttttt tttgaagtaa      900
tggagatgct ctaaggggag gtcattttct aaacaaattt aagaataaaa aaggaaaaca    960
caggagcagc tataggtaag gtgctataat cgaaaaataa ttgttgtact aggtagcatt   1020
cgaggagcat tttgtagcta gatgattaag gtaaaaaaag tgtgactgct gcggccaaag   1080
```

```
aagcatgcgc aaatctttct ctcggctccc tttgcatgca caacctactc gctaccttac    1140
cctcccgcta cctcgctcga tctgtgcatg cacaggtata tatatatacc tagctagctg    1200
ctagtttgtc gtcccagccc aggcatcgcc aagcaagtgg agtagtacg atg gtg atc    1258
                                                      Met Val Ile
                                                        1 aat agg ccg cag tta gtt tgt agt ata ata gtc tgt ttt gca act gct      1306
Asn Arg Pro Gln Leu Val Cys Ser Ile Ile Val Cys Phe Ala Thr Ala
  5                  10                  15 gtt ttg cac ctc cac                                                   1321
Val Leu His Leu His
 20
```

```
<210> SEQ ID NO 20
<211> LENGTH: 24
<212> TYPE: PRT
<213> ORGANISM: Zea mays

<400> SEQUENCE: 20

Met Val Ile Asn Arg Pro Gln Leu Val Cys Ser Ile Ile Val Cys Phe
 1               5                  10                  15

Ala Thr Ala Val Leu His Leu His
            20
```

```
<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
gtggagtagt accatggtga tc                                               22
```

```
<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
acctgctgtt ttgcacctcc ac                                               22
```

```
<210> SEQ ID NO 23
<211> LENGTH: 155
<212> TYPE: DNA
<213> ORGANISM: Zea mays

<400> SEQUENCE: 23
gaggcatcgc caagcaagtg gagtagtacg atggtgatca ataggccgca gttagtttct     60 agtataaatag tctgttttgc aacctgctgt tttgcacctc caccgcctat ccaccacatg   120
tatgttgaca tcactactca gacttacaat agttt                                155
```

```
<210> SEQ ID NO 24
<211> LENGTH: 42
<212> TYPE: PRT
<213> ORGANISM: Zea mays

<400> SEQUENCE: 24

Met Val Ile Asn Arg Pro Gln Leu Val Ser Ser Ile Ile Val Cys Phe
 1               5                  10                  15
```

```
Ala Thr Cys Cys Phe Ala Pro Pro Pro Ile His His Met Tyr Val
            20                  25                  30

Asp Ile Thr Thr Gln Thr Tyr Asn Ser Leu
        35                  40

<210> SEQ ID NO 25
<211> LENGTH: 269
<212> TYPE: DNA
<213> ORGANISM: Zea mays

<400> SEQUENCE: 25
caaaatgggg tgctgttgat ggtcgatata acagtatggc taagcatgtc caagaggcta      60
ttaatgtcaa tgatgcgaac gatgctttga caatcattga ttttctgctt cgcccaacag     120
aggaagtaga tactggtaat tagttttaat atatataatt attagttacg tcatcgatct     180
gttgtaatag tttatatata cctctaatat taaaaaagta aaatttcagc cttgtttcca     240
aaaaaaaaaa aaaaaaaaaa aaaaaaaaa                                        269

<210> SEQ ID NO 26
<211> LENGTH: 47
<212> TYPE: PRT
<213> ORGANISM: Zea mays

<400> SEQUENCE: 26

Pro Lys Trp Gly Ala Val Asp Gly Arg Tyr Asn Ser Met Ala Lys His
  1               5                  10                  15

Val Gln Glu Ala Ile Asn Val Asn Asp Ala Asn Asp Ala Leu Thr Ile
            20                  25                  30

Ile Asp Phe Leu Leu Arg Pro Thr Glu Glu Val Asp Thr Gly Asn
        35                  40                  45

<210> SEQ ID NO 27
<211> LENGTH: 28
<212> TYPE: DNA
<213> ORGANISM: Artificial Sequence
<220> FEATURE:
<223> OTHER INFORMATION: Primer

<400> SEQUENCE: 27
ggaagtagat actggtaatt accgcggc                                         28

<210> SEQ ID NO 28
<211> LENGTH: 1133
<212> TYPE: DNA
<213> ORGANISM: Zea mays
<220> FEATURE:
<221> NAME/KEY: CDS
<222> LOCATION: (586)..(900)

<400> SEQUENCE: 28
tacgggaccc atatttctac aggcggccct gctagtatac actatgtcta gatgtatagt      60
tgggtttaat ttgcattttg tcgggtttaa tttgcatttt ataatttaga acggaaggag     120
tagcattttg tcagtttaat tttcatttct ttgtgttagt tgggtgccca cgcatccaac     180
tcttcaagaa gctctttagt tgttagggac actggtactg tctgaaacat cgaactatct     240
ataagatttc atttcacaaa caaaacttgg gagtctccat tccaaccatc ctcgctcttt     300
ccattttcat ccggtcatcc ccctcgccct cctgctctt  ccagtttcaa gtttgaaccg     360
tcgcctttgg gaatcgagcc gtgggtccca ccttgtaaag aactgatcaa gccaatcgac     420
ttatcaacat cctcgctaca aatatccgcc accctaattt ggccaagcct tccaaacgaa     480
```

```
gaacaacaca atccaagagc gacgtgggag agcgagcgag aaagcaagat cgagagaaga      540
cgacacaaga agcaataaag agtcggggac cggagtgaag gaccg atg gcc gtc tac      597
                                                  Met Ala Val Tyr
                                                  1 ttc agc atc acc gcc ttc ctt gtc gtc atc atc ctg gtc ctg gcc gcg       645
Phe Ser Ile Thr Ala Phe Leu Val Val Ile Ile Leu Val Leu Ala Ala
 5              10                  15                  20 tgc ggc gtc gtt ttt gtc aat gtc gtc gtc atc ata tgg ggc ttc gcc       693
Cys Gly Val Val Phe Val Asn Val Val Val Ile Ile Trp Gly Phe Ala
                25                  30                  35 ctc gcc gcg tct ccg ttc tcg ttc tta ctg tcc aag gtc aag tgg cat       741
Leu Ala Ala Ser Pro Phe Ser Phe Leu Leu Ser Lys Val Lys Trp His
            40                  45                  50 tcg cgg cca ccg cca tcg tca cgg acg tcg gag gag gag ttg atg ttt       789
Ser Arg Pro Pro Pro Ser Ser Arg Thr Ser Glu Glu Glu Leu Met Phe
        55                  60                  65 cca tcg cac tgg ttc gac gaa aca cta ctg cag gcg gac tcg gag gag       837
Pro Ser His Trp Phe Asp Glu Thr Leu Leu Gln Ala Asp Ser Glu Glu
    70                  75                  80 gag gtc ctg ctt ccg acg cac tgg ttc gac gaa aca cta ttg cag gag       885
Glu Val Leu Leu Pro Thr His Trp Phe Asp Glu Thr Leu Leu Gln Glu
85                  90                  95                 100 tct cca tcg cag tag acaggcgtga tcgagcttgg acgtgacgga gttgacgcgt       940
Ser Pro Ser Gln cctttggggc ggtctggatc agttcttgtt ctagaagttg aatgattctt tcgacgtttc     1000
tgtcactgca ttttttggaa ctgatcaagg gtagtatgct ggtgcgtgtc gcctgatagt     1060
ctagattagt cattgaaaca ttttccatt gtttctgcca ttcgctttct tggaaactat      1120
cgagcttagc tgc                                                        1133

<210> SEQ ID NO 29
<211> LENGTH: 104
<212> TYPE: PRT
<213> ORGANISM: Zea mays

<400> SEQUENCE: 29

Met Ala Val Tyr Phe Ser Ile Thr Ala Phe Leu Val Val Ile Ile Leu
1               5                   10                  15

Val Leu Ala Ala Cys Gly Val Val Phe Val Asn Val Val Val Ile Ile
                20                  25                  30

Trp Gly Phe Ala Leu Ala Ala Ser Pro Phe Ser Phe Leu Leu Ser Lys
            35                  40                  45

Val Lys Trp His Ser Arg Pro Pro Ser Ser Arg Thr Ser Glu Glu
    50                  55                  60

Glu Leu Met Phe Pro Ser His Trp Phe Asp Glu Thr Leu Leu Gln Ala
65                  70                  75                  80

Asp Ser Glu Glu Glu Val Leu Leu Pro Thr His Trp Phe Asp Glu Thr
                85                  90                  95

Leu Leu Gln Glu Ser Pro Ser Gln
                100
```